US012788030B2

(12) United States Patent
Tran et al.

(10) Patent No.: US 12,788,030 B2
(45) Date of Patent: Nov. 10, 2026

(54) PRODUCTS AND METHODS FOR INHIBITING RESPIRATORY CONDITIONS

(71) Applicant: Purina Animal Nutrition LLC, Arden Hills, MN (US)

(72) Inventors: Huyen T. Tran, Lincoln, NE (US); Brenda de Rodas, O'Fallon, MO (US); Theodore P. Karnezos, Colchester, VT (US); Diana Ayala, Ballwin, MO (US)

(73) Assignee: Purina Animal Nutrition LLC, Arden Hills, MN (US)

(*) Notice: Subject to any disclaimer, the term of this patent is extended or adjusted under 35 U.S.C. 154(b) by 227 days.

(21) Appl. No.: 17/393,131

(22) Filed: Aug. 3, 2021

(65) Prior Publication Data

US 2023/0058302 A1 Feb. 23, 2023

(51) Int. Cl.
*A23K 10/18* (2016.01)
*A23K 10/30* (2016.01)
(Continued)

(52) U.S. Cl.
CPC .............. *A23K 10/18* (2016.05); *A23K 10/30* (2016.05); *A23K 50/10* (2016.05); *A23K 50/30* (2016.05);
(Continued)

(58) Field of Classification Search
CPC ........ A23K 10/18; A23K 10/26; A23K 10/30; A23K 50/10; A23K 50/30; A23K 50/75;
(Continued)

(56) References Cited

U.S. PATENT DOCUMENTS

| | | | |
|---|---|---|---|
| 2,125,398 | A | 8/1938 | Reichert et al. |
| 4,378,376 | A | 3/1983 | Wagner et al. |

(Continued)

FOREIGN PATENT DOCUMENTS

| | | | |
|---|---|---|---|
| CA | 2323581 | A1 | 10/1999 |
| CN | 101049116 | A | 10/2007 |

(Continued)

OTHER PUBLICATIONS

Mingmongkolchai S, Panbangred W. Bacillus probiotics: an alternative to antibiotics for livestock production. J Appl Microbiol. Jun. 2018;124(6):1334-1346. doi: 10.1111/jam.13690. (Year: 2018).*

(Continued)

*Primary Examiner* — Michele L Jacobson
*Assistant Examiner* — Carrie Glimm
(74) *Attorney, Agent, or Firm* — Dorsey & Whitney LLP

(57) ABSTRACT

The present disclosure describes products formulated to inhibit respiratory conditions and symptoms in animals, along with associated methods of providing such products to the animals. Feeding methods involve providing animals with a feed product that includes a direct-fed microbial composition, at least one phytogenic compound, and/or at least one vitamin. The direct-fed microbial composition includes one or more strains of *Bacillus*. The animals can include swine or cattle at risk of developing, or already afflicted with, a respiratory condition. Inhibition of respiratory stress can reduce mortality rates and medication administration relative to animals fed the same diet but lacking the feed product.

7 Claims, 3 Drawing Sheets

(51) Int. Cl.

| | |
|---|---|
| ***A23K 50/10*** | (2016.01) |
| ***A23K 50/30*** | (2016.01) |
| ***A61K 31/593*** | (2006.01) |
| ***A61K 35/742*** | (2015.01) |
| ***A61K 36/81*** | (2006.01) |
| ***A61K 36/9066*** | (2006.01) |
| ***A61P 31/04*** | (2006.01) |

(52) U.S. Cl.
CPC .......... *A61K 31/593* (2013.01); *A61K 35/742* (2013.01); *A61K 36/81* (2013.01); *A61K 36/9066* (2013.01); *A61P 31/04* (2018.01)

(58) Field of Classification Search
CPC .... A23K 10/38; A23K 20/111; A23K 20/147; A23K 20/163; A23K 20/174; A23K 40/30; A61K 31/375; A61K 31/593; A61K 35/742; A61K 36/752; A61K 36/81; A61K 36/9066; A61K 36/48; A61K 36/53; A61K 36/61; A61K 36/73; A61P 31/04
See application file for complete search history.

(56) References Cited

U.S. PATENT DOCUMENTS

| | | | |
|---|---|---|---|
| 4,617,190 | A | 10/1986 | Montgomery |
| 4,961,934 | A | 10/1990 | Iwasaki et al. |
| 5,085,873 | A | 2/1992 | Degre |
| 5,580,592 | A | 12/1996 | Nassauer et al. |
| 5,607,681 | A | 3/1997 | Galley et al. |
| 5,668,299 | A | 9/1997 | Debonte et al. |
| 5,681,856 | A | 10/1997 | Brinton |
| 5,747,078 | A | 5/1998 | De et al. |
| 5,756,132 | A | 5/1998 | Rebhan |
| 5,785,990 | A | 7/1998 | Langrehr |
| 5,792,501 | A | 8/1998 | Lepin |
| 5,795,602 | A | 8/1998 | Craig et al. |
| 5,830,511 | A | 11/1998 | Mullerat et al. |
| 5,861,187 | A | 1/1999 | Debonte et al. |
| 5,962,062 | A | 10/1999 | Carrie et al. |
| 6,348,223 | B1 | 2/2002 | Claycamp et al. |
| 6,365,152 | B1 | 4/2002 | Mckinney |
| 6,500,426 | B1 | 12/2002 | Barendse et al. |
| 6,541,047 | B1 | 4/2003 | Claycamp et al. |
| 6,562,340 | B1 | 5/2003 | Bedford et al. |
| 7,247,299 | B2 | 7/2007 | Lin et al. |
| 7,384,628 | B2 | 6/2008 | Rehberger et al. |
| 7,709,033 | B2 | 5/2010 | Kvist et al. |
| RE43,929 | E | 1/2013 | Miller et al. |
| 8,349,313 | B2 | 1/2013 | Smith et al. |
| 8,540,981 | B1 | 9/2013 | Wehnes et al. |
| 8,603,551 | B1 | 12/2013 | Novak et al. |
| 9,113,642 | B2 | 8/2015 | Kanbe et al. |
| 9,179,693 | B2 | 11/2015 | Romero et al. |
| 9,487,749 | B2 | 11/2016 | Benjamin et al. |
| 10,940,172 | B2 | 3/2021 | Caldwell et al. |
| 2002/0018828 | A1 | 2/2002 | Lepine |
| 2002/0048607 | A1 | 4/2002 | Muscato et al. |
| 2002/0119136 | A1 | 8/2002 | Johansen |
| 2005/0106163 | A1 | 5/2005 | David et al. |
| 2005/0171367 | A1 | 8/2005 | Deloach |
| 2006/0159728 | A1 | 7/2006 | Miller |
| 2006/0289354 | A1 | 12/2006 | Zhou et al. |
| 2007/0036850 | A1 | 2/2007 | Roehrich et al. |
| 2007/0134369 | A1 | 6/2007 | Mazeris |
| 2007/0203802 | A1 | 8/2007 | Medo et al. |
| 2007/0209599 | A1 | 9/2007 | Block et al. |
| 2008/0026036 | A1 | 1/2008 | Miller et al. |
| 2008/0026101 | A1 | 1/2008 | Nickel et al. |
| 2008/0057047 | A1 | 3/2008 | Sas et al. |
| 2008/0118615 | A1 | 5/2008 | Hartmann et al. |
| 2009/0253790 | A1 | 10/2009 | Smith et al. |
| 2009/0280090 | A1 | 11/2009 | Rehberger et al. |
| 2009/0317378 | A1 | 12/2009 | Perraudin |
| 2010/0221386 | A1 | 9/2010 | Buysse et al. |
| 2011/0201081 | A1 | 8/2011 | Kensch et al. |
| 2011/0229598 | A1 | 9/2011 | Musser |
| 2012/0321592 | A1 | 12/2012 | Schmidt et al. |
| 2013/0280369 | A1 | 10/2013 | Miller |
| 2013/0330308 | A1 | 12/2013 | Millan et al. |
| 2014/0147548 | A1 | 5/2014 | Miller et al. |
| 2014/0336271 | A1 | 11/2014 | Moore et al. |
| 2015/0374740 | A1 | 12/2015 | Forsberg et al. |
| 2016/0205970 | A1 | 7/2016 | Bruggeman et al. |
| 2016/0206654 | A1 * | 7/2016 | Sandberg ............. A61K 31/165 |
| 2016/0213029 | A1 | 7/2016 | Bruggeman et al. |
| 2016/0250239 | A1 | 9/2016 | Bruggeman et al. |
| 2016/0280778 | A1 | 9/2016 | Cook et al. |
| 2017/0202928 | A1 | 7/2017 | Miller et al. |
| 2017/0231254 | A1 | 8/2017 | Miller |
| 2018/0185425 | A1 | 7/2018 | Caldwell et al. |
| 2018/0228181 | A1 | 8/2018 | Rodríguez Villamizar et al. |
| 2019/0289878 | A1 | 9/2019 | Miller et al. |
| 2020/0276279 | A1 | 9/2020 | Millan et al. |
| 2020/0359653 | A1 * | 11/2020 | Johnson ................. A23K 10/18 |

FOREIGN PATENT DOCUMENTS

| | | | | |
|---|---|---|---|---|
| CN | 101703171 | A | 5/2010 | |
| CN | 101911981 | A | 12/2010 | |
| CN | 102132766 | A | 7/2011 | |
| CN | 102805263 | A | 12/2012 | |
| CN | 103271091 | A | 9/2013 | |
| CN | 104621047 | A | 5/2015 | |
| CN | 104762224 | A | 7/2015 | |
| CN | 106260523 | A | 1/2017 | |
| EP | 0229938 | A1 | 7/1987 | |
| EP | 0282663 | B1 | 12/1991 | |
| EP | 0642740 | B1 | 3/1995 | |
| EP | 1637880 | A1 | 3/2006 | |
| EP | 1815754 | A1 | 8/2007 | |
| JP | 2509932 | Y2 | 2/1990 | |
| JP | H0789863 | | 10/1995 | |
| JP | 3145829 | U | 3/2001 | |
| JP | 2002544212 | A | 12/2002 | |
| JP | 2004236552 | A | 8/2004 | |
| KR | 20100101091 | A | 9/2010 | |
| KR | 101272140 | B1 | 6/2013 | |
| WO | 9949740 | A1 | 10/1999 | |
| WO | 0069267 | A1 | 11/2000 | |
| WO | 02056879 | A1 | 7/2002 | |
| WO | 2007015937 | A1 | 2/2007 | |
| WO | 2007064741 | A2 | 6/2007 | |
| WO | 2007106452 | A2 | 9/2007 | |
| WO | 2010033714 | A1 | 3/2010 | |
| WO | WO-2010139726 | A1 * | 12/2010 | ............. A23K 10/18 |
| WO | 2011055387 | A2 | 5/2011 | |
| WO | 2011061756 | A2 | 5/2011 | |
| WO | 2011115306 | A1 | 9/2011 | |
| WO | 2012110777 | A2 | 8/2012 | |
| WO | 2014020141 | A1 | 2/2014 | |
| WO | 2015160818 | A1 | 10/2015 | |
| WO | 2016060934 | A1 | 4/2016 | |
| WO | 2016118840 | A1 | 7/2016 | |
| WO | 2017025772 | A1 | 2/2017 | |
| WO | 2018148563 | A1 | 8/2018 | |

OTHER PUBLICATIONS

Ahmadu et al. "An Overview of Vitamin C as an Antistress in Poultry." Malaysian Journal of Veterinary Research, vol. 7, No. 2, Jul. 2016, pp. 9-22, http://www.poultrydvm.com/drugs/ascorbic-acid#:~:text=Dosage,to%20their%20diet%20per%20day (Year: 2016).*

Yen (Effect of dietary vitamin C addition on performance, plasma vitamin C and hematic iron status in weanling pigs. J Anim Sci. Nov. 1981;53(5):1292-6. doi: 10.2527/jas1981.5351292x.) (Year: 1981).*

Dang (Dang, D. X., & Kim, I. H. (2020). Effects of dietary supplementation of Quillaja saponin on growth performance, nutrient digestibility, fecal gas emissions, and meat quality in finishing

(56) References Cited

OTHER PUBLICATIONS pigs. Journal of Applied Animal Research, 48(1), 397-401. https://doi.org/10.1080/09712119.2020.1813739.) (Year: 2020).*
International Search Report and Written Opinion issued in International Application No. PCT/US2022/039039, mailed on Oct. 13, 2022, 8 pages.
Villarroel, "Scours in Beef Calves: Causes and Treatments", EM 8977-E, 5 pages, Apr. 2009, Oregon State University, retrieved from https://catalog.extension.oregonstate.edu/em8977.
PCT International Search Report mailed Jun. 25, 2019 in PCT Application No. PCT/US2019/023641.
PCT Written Opinion mailed Jun. 25, 2019 in PCT Application No. PCT/US2019/023641.
"Jersey Blend—Cow's match—Calf growth formula", Jan. 1, 2004 (Jan. 1, 2004), Mar. 2013, (Mar. 2013), XP55194288, Retrieved from the Internet:URL:http://www.lolmilkreplacer.com/stellen/groups/public/documents/web_content/ecmp2-0186429.pdf, 2 pages.
"Nursing Formula Select", Available online at www.masterfeeds.com on Sep. 2, 2011, 3 pages.
Agazzi, et al., "Effects of species-specific probiotic addition to milk replacer on calf health and performance during the first month of life", Ann. Anim. Sci., vol. 14, No. 1, 2014, 101-115.
Barabas, "An alternative method of milk treatment", http://www.fao.org/ag/aga/frg/feedback/war/v6200b/v6200b0t. htm, Sep. 13, 1994, 5 pages.
Bayatkouhsar, et al., "Effects of supplementation of lactic acid bacteria on growth performance, blood metabolites and fecal coliform and lactobacilli of young dairy calves", Animal Feed Science and Technology, vol. 186, Issues 1-2, Nov. 15, 2013, pp. 1-11.
Better Crops, "Phosphorus in Animal Nutrition", Better Crops; vol. 83. No. 1, 1999, pp. 32-33.
Bovine Alliance on Managem., & Nutrition, "A Guide to Calf Milk Replacers—Types, Use and Quality", 2008, 4 pages.
Broadway, et al., "The Effects of the Dfm Clostat (R) adn Experimental *Salmonella* Challenge on the Microbiome of the Ileum in Weaned Holstein Steer Calves", Journal of Animal Science, 96 (suppl): 41-42, Mar. 1, 2018.
Calf Sessions, "The Science of Mixing Milk Replacer", http://calfsessions.com/2013/06/science-mixing-milk-replacer-rnixology-101/, 2013, 5 pages.
Campbell, et al., "The use of lactoperoxidase for the bleaching of fluid whey", Journal of Dairy Science, 2012, 95.6 pp. 2882-2890.
Connor, "α-Linolenic acid in health and disease", Am. J Clin. Nutr; vol. 69, 1999, pp. 827-828.
Costello, "Milk Extenders and Fortifiers—with downloadable calculator", Available online at www.calfsessions.com, Jan. 2015, 2 pages.
Coverdale, et al., "Effect of Various Levels of Forage and Form of Diet on Rumen Development and Growth in Calves", J. Dairy Sci.; vol. 87, 2004, pp. 2554-2562.
Crews, et al., "Journal of Animal Science", Animal Genetics: Division Editor Cell Biology S. Ellis Associate Editor Growth and Developmental Biology S. Johnson Calvert Associate Editor M. Estienne Associate Editor J. Matte Associate Editor J. O'Doherty, XP055426140,, Retrieved from the Internet: URL:http://www.jtmtg.org/JAM/2012/abstracts/2012-JAMAbstracts.pdf [retrieved on Nov. 17, 2017], Jan. 1, 2012, p. 116.
Crowder, "The Effect of Medium Chain Fatty Acids on Porcine Reproductive and Respiratory Syndrome Virus", dissertation, May 2021, 149 pages, Purdue University, department of Animal Sciences, West Lafayette, Indiana.
Database Caplus [Online], Chemical Abstracts Service, Columbus, Ohio, US; 2014, XP002791790, database accession No. 2015:1332789, Liu, J. et al.: "Effects of Bacillus subtilis (PB6 strain) additive on reproduction of weaning piglet," Xumu Yu Shouyi, vol. 46, No. 2, pp. 37-39, 2014.
De Halleux, et al., "Variability in human milk composition: benefit of individualized fortification in very-low-birth-weight infants'", The American Jrnl of Clinical Nutrition; vol. 98 (Suppl), 2013, pp. 529S-535S.
De Rodas, et al., "Microbiome Profiling of Commercial Pigs from Farrow to Finish", American Society of Animal Sciences, vol. 96, pp. 1778-1794, 2018, Oxford University Press.
Dimova, et al., "Effect of supplementation of probiotic zoovit in diets of calves of milk breed", Bulgarian Journal of Agricultural Science, 19 (Supplement 1), Jan. 2013, 94-97.
Drackley, "Replacing Milk-Derived Proteins and Carbohydrates in Milk Replacer", University of Illinois at Urbana-Champaign, Department of Animal Sciences, May 29, 2013, 8 pages.
Dumitrascu, et al., "Thermal Inactivation of Lactoperoxidase in Goat, Sheep and Bovine Milk—A Comparative Kinetic and Thermodynamic Study", Journal of Food Engineering, 2012, vol. 113 pp. 47-52.
Echternkamp, "Relationship between placental development and calf birth weight in beef cattle", Animal Reproduction Science, 32: 1-13, 1993.
Elizondo-Salazar, et al., "Pasteurization of Non-Saleable Milk", Penn State Extension, Department of Animal Science, DSE 2013-187, originally published as DAS 07-121, updated on Aug. 23, 2013, May 2007, 10 pages.
EPO, "Extended European Search Report", Application No. 17161383.9, May 2, 2017, 35 pages.
EPO, "Extended European Search Report", Patent Application No. 15159436.3, Jun. 26, 2015, 9 pages.
EURASYP, "Yeast Cell Wall", European Association for Specialty Yeast Products, Nov. 5, 2015, 1 page.
Euro Food Safety Auth., "Scientific opinion on the safety and efficacy of RonozymeHiPhos M/L (6-phytase) as a feed additive for poultry and pigs", EFSA Journal; 10(1):2527, 2012, 12 pages.
FAO Animal Production and Health, "Rearing Young Ruminants on Milk Replacers and Starter Feeds", 2011, 1-79.
Fathi, et al., "The effect of vanilla flavoured calf starter on performance of Holstein calves", Jrnl. of Animal and Feed Sci.; Vo. 18, 2009, pp. 412-419.
Frizzo, et al., "Effects of probiotics on growth performance in young calves: A meta-analysis of randomized controlled trials", Animal Feed Science and Technology 169, 2011, 147-156.
Frizzo, et al., "Lactic acid bacteria to improve growth performance in young calves fed milk replacer and spray-dried whey powder", Animal Feed Science and Technology 157 (2010) 159-167.
Frontline, "Use of the Brix Refractometer for Monitoring Milk Total Solids and Colostrum Quality", www.rnilkproductsinc.com; Accessed on Dec. 5, 2011, 1 page.
Godden, "A review of issues surrounding the feeding of waste milk and pasteurization of waste milk and colostrum", College of Veterinary Medicine, University of Minnesota, Sep. 2005, 13 pages.
Gouveia, et al., "Action of phosphorylated mannanoligosaccharides on immune and hematological responses and fecal consistency of dogs experimentally infected with enteropathogenic *Escherichia coli* strains", Brazilian Jrnl. of Microbiology; vol. 44 No. 2, 2013, pp. 499-504.
Griffiths, "Improving the Safety and Quality of Milk: Milk Production and Processing Woodhead Publishing Series in Food ScienceTechnology and Nutrition", Apr. 21, 2010, 295 pages.
Heinrichs, et al., "Effects of Mannan Oligosaccharide or Antibiotics in Neonata Diets on Health and Growth of Dairy Calves", Jrnl. of Dairy Sci.; vol. 86 No. 12, Dec. 2003, pp. 4064-4069.
Hill, et al., "Effects of Milk Replacer Composition on Growth, Body Composition, and Nutrient Excretion in Preweaned Holstein Heifers", Jrnl. of Dairy Sci., Amer. Dairy Sci. Assoc.; vol. 91 No. 8, Aug. 1, 2008, pp. 3145-3155.
Hu, et al., "Effects of intrauterine growth retardation and Bacillus subtilisPB6 supplementation on growth performance, intestinal development and immune function of piglets during the suckling period", European Journal of Nutrition, Steinkopff Verlag, Darmstadt, DE, 56(4): 1753-1765, May 17, 2016.
Industries Kemin, "Clostat(R) product specification", Retrieved from the Internet: URL:https://www.kemin.com/content/dam/images/CLOSTAT%20Dry%20Spec%20Sheet.pdf [retrieved on Jun. 2019], Jan. 1, 2017.
Jackett, et al., "Virulence of *Mycobacterium tuberculosis* and Susceptibility to Peroxidative Killing Systems", Journal of General Microbiology; vol. 107 No. 2, pp. 273-278.

(56) References Cited

OTHER PUBLICATIONS

Jatkauskas, et al., "Effects of a Combined Pre- and Probiotics Product on Diarrhoea Patterns and Performance of Early Weaned Calves", ISSN 1392-2130. Veterinarija Ir Zootechnika (Vet Med Zoot). T. 48 (70). 2009, 17-23.
Jatkauskas, et al., "Effects of Encapsulated Probiotic Enterococcus Faeciumstrain on", ISSN 1392-2130. Veterinarija Ir Zootechnika (Vet Med Zoot). T. 67 (89)., 2014, 47-52.
Jorgensen, et al., "On-Farm Pasteurization of Milk for Calves", University of Wisconsin Dail)' Update, Dail)' Team Extension, Mar. 31, 2005, pp. 1-3.
Kemin North America, "Clostat® Product Sheet", downloaded from https://www.kemin.com/en/north-america/products/clostat on Feb. 15, 2018, 7 pages.
Land O'Lakes, "Pasteurized Milk Balancer", https://s3.amazonaws.com, 2009, 1 page.
Langendijk, et al., "Effects of pre- and postnatal exposure to garlic and aniseed flavour on pre- and postweaning feed intake in pigs", Livestock Science, Elsevier Amsterdam, NL; vol. 108 No. 1-3, Apr. 29, 2007, pp. 284-287.
Mexican Institute of IP, "Mexican Patent Examination Report", Patent Application No. MX/a/2012/010741, Mar. 6, 2015, 16 pages.
MIA-A, "Milk Analyzer Operation Manual", https://www.mrclab.com/data/products/MIA-S-30_0PR.pdf, 2005, 100 pages.
Milk Specialties Global, Naimal Nutrition , "New Dairy Calf Production Products that can Increase Your Profit", PM Primer™, PM Balancer™ downloaded from www.progressivedairy.com on Mar. 5, 2015., 1 page.
Mitsuru, et al., "Effects of feeding level of milk replacer on body growth, plasma metabolite and insulin concentrations, and visceral organ growth of suckling calves", Anim. Sci. Jrnl. XP055194192, ISSN: 1344-3941, DOI: 10.1111/j.1740-0929.2009.00690.x; vol. 80 No. 6, Dec. 2009, pp. 662-668.
Montoro, et al., "Effect of flavoring a starter in a same manner as a milk replacer on intake and performance of calves", Animal Feed Sci. and Technol.; vol. 164, Feb. 28, 2011, pp. 130-134.
Moore, et al., "Quality assessments of waste milk at a calf ranch", J. Dairy Sci; vol. 92, 2009, pp. 3503-3509.
Mullan, "Manufacture of milk powders containing a functional LP system", [Online]. Available from: htt.Q://www.dairyscience.info/exploitation-of-ant-microbial-proteins/168-lactoperoxidase-system.html. Accessed: Jan. 10, 2014. Revised Aug. 2009, 2003, 4 pages.
Nabte-Solfs, "Effect of 13-Mannanase Enzyme Addition to Soy-Containing Milk Replacers on Growth and Health of Neonatal Dairy Calves", Thesis Presented to the Faculty of the Graduate School of Cornell University, Jan. 2009, 105 pages.
Oostindjer, et al., "Prenatal flavor exposure affects growth, health and behavior of newly weaned piglets", Physiology and Behavior, Elsevier Science Ltd., Oxford, GB,; vol. 99 No. 5, Apr. 19, 2010, pp. 579-586.
PCT, "International Search Report and Written Opinion", Application No. PCT/US2016/019848, May 12, 2016, 10 pages.
PCT, "International Search Report and Written Opinion", Application No. PCT/US2016/021789, Jun. 3, 2016, 10 pages.
PCT, "International Search Report and Written Opinion", Application No. PCT/US2016/067683, Mar. 22, 2017, 8 pages.
PCT, "International Search Report and Written Opinion", Application No. PCT/US2015/038612, Sep. 23, 2015, 8 pages.
Pinchuk, et al., "In Vitro Anti-Helicobacter pylori Activity of the Probiotic Strain Bacillus subtilis 3 Is Due to Secretion of Antibiotics", Antimicrobial Agents and Chemotherapy, Nov. 2001, p. 3156-3161, vol. 45, No. 11.
Pruitt, et al., "Quantitative analysis of bovine lactoperoxidase system components and of tile effects of the activated system on bacterial growth and survival", Indigenous antimicrobial agents of milk. Recent developments, Uppsala (Sweden) Aug. 31-Sep. 1993, FIL-IDF. Secretariat general, 1994, pp. 73-87.
Rochow, et al., "Target Fortification of Breast Milk with Fat, Protein, and Carbohydrates for Preterm Infants", The Journal of Pediatrics; vol. 163 No. 4, 2013, pp. 001-1007.
Rudolph, "Phytase use in pig feed: a real profitability boost", All About Feed; vol. 22 No. 8, 2014, pp. 22-24.
Russell, et al., "Naturally Occurring Antimicrobial Systems", Food Preservatives 2nd Ed. ISBN 0-306-47736-X, 2003, pp. 277a-277b.
SAV-A-CAF Products, "K-Cal for Calves Energy Supplement", https://www.savacaf.com/products/k-cal-for-calves-energy-supplement/, 2007, 5 pages.
Sebastian, et al., "Apparent Digestibility of Protein and Amino Acids in Broiler Chickens Fed a Com-Soybean Diet Supplemented with Microbial Phytase", Dep. of Anim. Sci., Macdonald Campus of McGill University; vol. 76 No. 12, 1997, pp. 1760-1769.
Selia, et al., "Engineering Aspects of Milk and Dariy Products", CRC Press, 2010, pp. 222.
Siemens, et al., "Managing and feeding Holstein steers: birth to 350 lbs", US Dept. of Agriculture, Univ. of Wisconsin-Extension. Publ. A3662. Board of Regents of the Univ. of Wisconsin System, 1996, pp. 1-6.
Signorini, et al., "Impact of probiotic administration on the health and fecal microbiota of young calves: A meta-analysis of randomized controlled trials of lactic acid bacteria", Research in Veterinary Science 93, 2012, 250-258.
Smith, et al., "The Effect of Mannan Oligosaccharide Supplementation on Body Weight Gain and Fat Accrual in C57Bl/6J Mice", Obesity (Silver Spring), doi:10.1038/oby.2009.308: vol. 18 No. 5, May 2010, pp. 995-999.
Soca, et al., "Effect of the Sorbial® probiotic on the productive performance and health of grazing calves", Pastos y Forrajes vol. 34 No. 4 Matanzas Sep.-Dec. 2011.
Sorokulova, et al., "Probiotics against Campylobacter Pathogens", Journal of Travel Medicine, vol. 4, No. 4, 1997, 167-170.
Stone, "Waste milk, milk replacer or pasteurized waste milk", The Manager, Jun. 2004, 3 pages.
Tomkins, et al., "Milk replacer research leads to new developments", Feedstuffs, Oct. 10, 1994, pp. 13-15 and 23.
Touchette, et al., "Liquid Egg as an Alternative Protein Source in Calf Milk Replacers", J. Dairy Sci.; vol. 86, 2003, pp. 2622-2628.
Yang, et al., "Study on the Colostrum Preservation of Milk Cows by Utilizing the Lactoperoxidase System", Guizhou Agricultural Sciences, accessed Dec. 28, 2013., May 2007, 1 page.
Zhang, et al., "Effect of oral administration of probiotics on growth performance, apparent nutrient digestibility and stress-related indicators in Holstein calves", Journal of Animal Physiology and Animal Nutrition, vol. 100 (1) p. 33-38, Feb. 2016.
Chilean Patent Examination Report, issued by the National Institute of IP for Patent Application No. 2556-2012, Feb. 11, 2015, 16 pages including 8 pages of English translation.
"Milk Balancer Can Help When Feeding Wasting Milk", Dairy Business East, www.dairybusiness.com, Feb. 2015, p. 12.
"Manual on the Use of the LP-System in Milk Handling and Preservation," Food and Agriculture Organization of the United Nations, 1999, 36 pages, Rome, Italy, retrieved from https://www.fao.org/4/x0496e/x0496e00.pdf.
"How do you Convert from Molarity (m) to Parts Per Million (ppm) and mg/L?" Nexsens Technology retrieved from Internet Jun. 2016, 1 page.
EPO, "European Office Action", Application No. EP13731012.4, Nov. 22, 2017, 6 pages.

* cited by examiner

300

PRODUCTS AND METHODS FOR INHIBITING RESPIRATORY CONDITIONS

TECHNICAL FIELD

The present disclosure relates to feed products and methods for inhibiting respiratory conditions in animals. Particular implementations include feed products containing direct-fed microbials and phytogenic compositions, along with associated methods of feeding that prevent and treat respiratory conditions.

BACKGROUND

Respiratory health is a significant priority for animal producers. Respiratory ailments, which may be caused at least in part by a large variety of bacterial pathogens, can negatively impact overall animal health and performance and increase mortality rates, all of which may reduce total production yield. The need for repeated medical intervention to prevent and treat respiratory conditions is costly and often ineffective. Traditional methods of combating respiratory infections, for example, have involved employing various antibiotics at therapeutic and sub-therapeutic doses; however, challenges with antibiotic resistance and negative public perceptions of antibiotic use are making such conditions more difficult to address. New approaches for combating respiratory stress are needed.

SUMMARY

The disclosed feed compositions and associated feeding methods may effectively inhibit a respiratory condition and associated symptoms. In accordance with some examples of the present disclosure, a method of feeding livestock animals may involve feeding the livestock animals a feed composition comprising a direct-fed microbial composition and a phytogenic composition, and optionally a vitamin composition. The direct-fed microbial composition can include two or more strains of *Bacillus* selected from strains of *Bacillus pumilus, Bacillus subtilis*, and *Bacillus amyloliquefaciens*. The phytogenic composition can include one or more phytogenic compounds of: quillaja, a citrus flavonoid, curcuma, capsicum, thymol essential oil, and eugenol essential oil. The optional vitamin composition can include one or more forms of vitamin C and/or vitamin D.

In some examples, the two or more strains of *Bacillus* are included in approximately equal amounts. In some examples, the phytogenic composition includes two or more of the phytogenic compounds. In some examples, the livestock animals include swine, cattle, or poultry. In some examples, the feed composition further includes one or more of: ground corn, sugar, dehulled soymeal, soy isolate, hydrolyzed soy protein, dried distillers grains with solubles, poultry byproduct meal, vitamins or minerals. In some examples, the direct-fed microbial composition and the phytogenic composition together constitute about 0.01 wt % to about 0.5 wt % of the feed composition.

In accordance with some examples of the present disclosure, a feed product formulated for livestock animals includes a complete base feed comprising one or more of: ground corn, sugar, dehulled soymeal, soy isolate, hydrolyzed soy protein, dried distillers grains with solubles, poultry byproduct meal, vitamins or minerals. The feed product further includes at least one direct-fed microbial comprising two or more strains of *Bacillus* selected from strains of *Bacillus pumilus, Bacillus subtilis*, and/or *Bacillus amyloliquefaciens*. The feed product further includes a phytogenic blend comprising two or more of quillaja, a citrus flavonoid, curcuma, capsicum, and an essential oil. In some embodiments, the feed product also includes one or more forms of vitamin C and/or D.

In some examples, the direct-fed microbial(s), the phytogenic blend, and the one or more forms of vitamin C and/or D together constitute about 0.01 wt % to about 0.5 wt % of the feed product. In some examples, the two or more strains of *Bacillus* are included in approximately equal amounts.

In accordance with some examples of the present disclosure, a method of inhibiting *Streptococcus* in animals involves introducing a direct-fed microbial and phytogenic composition to animal feed or feed ingredients. The direct-fed microbial in the composition can include two or more strains of *Bacillus*. The two or more strains of *Bacillus* can include strains of *Bacillus pumilus, Bacillus subtilis*, and/or *Bacillus amyloliquefaciens*. The phytogenic in the composition can include two or more of: quillaja, one or more citrus flavonoids, curcuma, capsicum, thymol essential oil, and eugenol essential oil. The direct-fed microbial and phytogenic composition can be introduced at an inclusion rate of from about 0.01 weight % to about 0.5 weight %.

In some examples, the two or more strains of *Bacillus* are included in approximately equal amounts. In some examples, the direct-fed microbial and phytogenic composition excludes antibiotics. In some examples, the feed or feed ingredients comprise a dry base feed or a liquid composition, the liquid composition comprising drinking water or a milk replacer.

In accordance with some examples of the present disclosure, a method of inhibiting respiratory stress in animals involves feeding the animals a feed product comprising a direct-fed microbial composition and a phytogenic composition, and optionally a vitamin composition. The direct-fed microbial composition can be present in an amount of at least 50 wt % of the feed product. In some examples, the phytogenic composition comprises one or more of quillaja, one or more citrus flavonoids, curcuma, capsicum, thymol essential oil, and eugenol essential oil. The feed product can be fed in an amount effective to inhibit respiratory stress.

In some examples, the direct-fed microbial composition includes two or more strains of *Bacillus* included in approximately equal amounts. In some examples, the two or more strains of *Bacillus* comprise strains of *Bacillus pumilus, Bacillus subtilis*, and/or *Bacillus amyloliquefaciens*. In some examples, inhibiting respiratory stress comprises preventing and/or alleviating a respiratory condition and/or a symptom thereof. In some examples, methods further involve combining the feed product with a feed composition to form a feed mixture. The feed composition can comprise one or more of: ground corn, sugar, dehulled soymeal, soy isolate, hydrolyzed soy protein, dried distillers grains with solubles, poultry byproduct meal, vitamins or minerals. In some examples, the feed product constitutes about 0.01 wt % to about 0.5 wt % of the feed mixture. The feed product may exclude antibiotics in some implementations.

DETAILED DESCRIPTION

Figure 1:
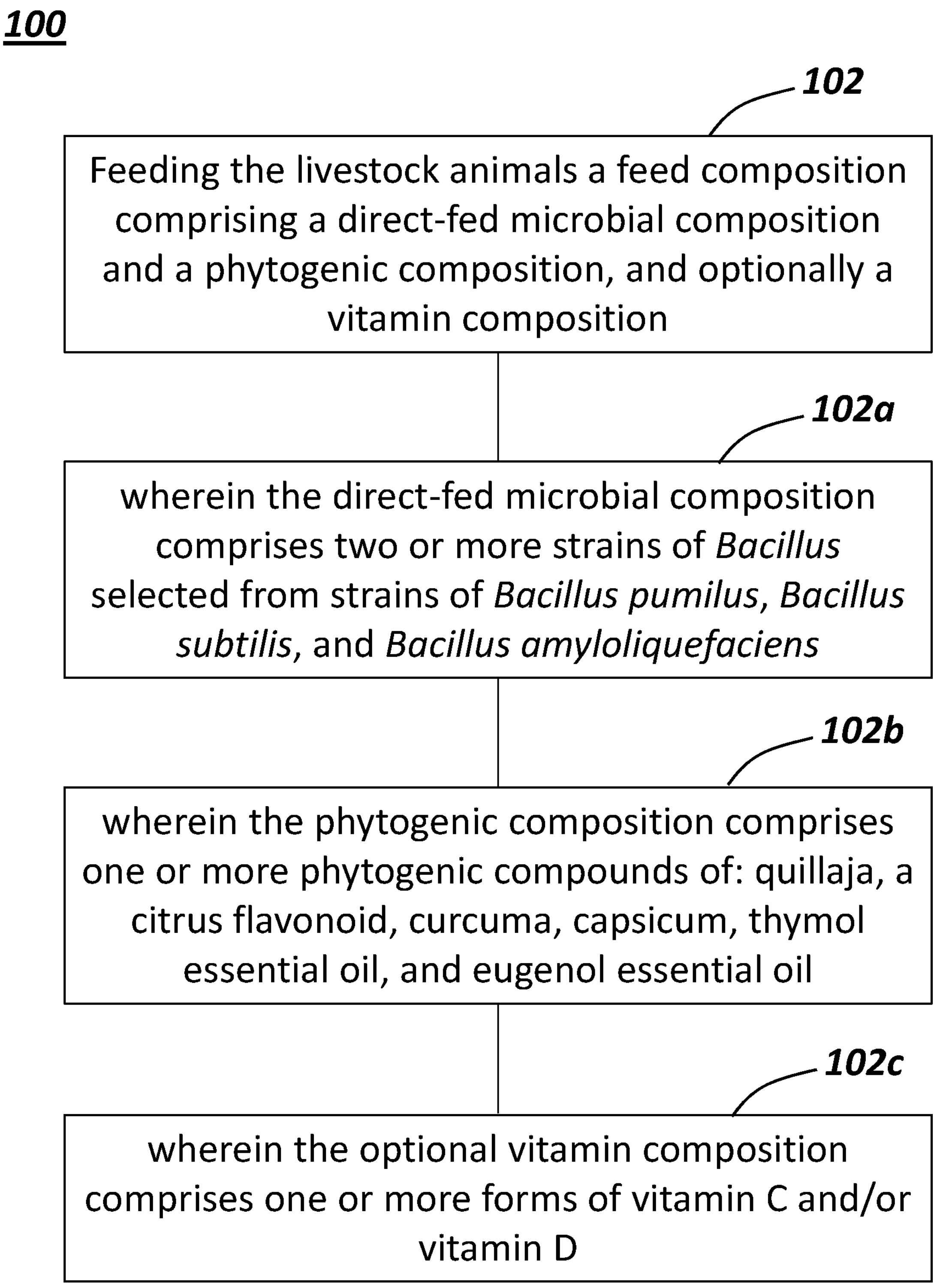
FIG. 1 is a flow chart showing a method of feeding livestock animals according to embodiments of the present disclosure.

Implementations provide methods of inhibiting respiratory stress conditions in animals by orally administering or feeding the animals a feed product containing one or more direct-fed microbials (DFMs), which are live microorganisms, along with at least one phytogenic compound. The feed product, which may also include various vitamins, can be a stand-alone product, a product formulated for mixing with base feed or liquid, and/or an integral component of a base feed or liquid. The DFMs included in the feed product can comprise one or more species of *Bacillus* in some embodiments, and the phytogenic compounds can include quillaja, curcuma, and/or capsicum, just to name a few. The animals offered the feed products disclosed herein can include various livestock animals, such as swine or cattle, of various ages. The feed products can be administered before or after the animals exhibit symptoms indicative of a respiratory condition, such as coughing or labored breathing. By not relying on the use of harmful chemicals and antibiotics, the disclosed feed products and associated methods provide safe, natural alternatives to preexisting approaches of inhibiting respiratory stress conditions. Embodiments may also be more effective than traditional respiratory treatment approaches, evidenced by the significant improvements in animal health achieved upon implementation of the disclosed methods.

Animal species fed the feed products disclosed herein may vary, and may include a variety of animals including animals housed in group settings, such as in farms or research facilities, animals housed individually, and animals susceptible to respiratory infections such as animals fed during seasonal changes, or during fall, winter, or spring; and sick animals. Such animals may include livestock, such as swine raised for pork production or ruminants such as those raised for dairy and/or beef production, including but not limited to young animals including piglets, calves, and mature animals including sows, boars, heifers, cattle, including lactating sows and ruminants. Equines including young equine animals (e.g., foals), companion animals (e.g., pets), zoo animals including young zoo animals, exotic animals including young exotic animals, and poultry including young poultry (e.g., chicks) may also be treated by the methods disclosed herein. Some embodiments may be specific to swine. Solely for ease of illustration and to encompass all contemplated target animals, this disclosure refers simply to "animals" as the beneficiaries of the disclosed feed products and associated methods.

The disclosed feed products and feeding methods are effective to inhibit one or more respiratory conditions or symptoms associated therewith. As used herein, "inhibition" may encompass the prevention, control, reduction, or elimination of a bacterial infection that causes a respiratory condition. For example, inhibition may refer to a reduction in the measurable levels of one or more bacterial pathogens or a decrease in the growth rate of such bacterial pathogens relative to an untreated control. Inhibition may also encompass treatment of a respiratory condition evidenced by a reduction in the severity, duration, and/or number of symptoms exhibited by an animal diagnosed with the condition. Inhibition may also include a cure for a respiratory condition, or a reduction or elimination of one or more associated symptoms, e.g., coughing, panting, or shallow breathing. Inhibition can encompass the prevention of a respiratory condition, especially for animals at a heightened risk of contracting it, for example animals not diagnosed with or currently exhibiting respiratory symptoms, but exposed to bacteria commonly associated with respiratory conditions. At-risk target animals can also include animals maintained in a setting where the incidence of respiratory conditions is moderate or high, and/or animals kept in a location where weather conditions are more favorable to the development of respiratory conditions. At-risk target animals can also include otherwise stressed animals and/or animals with compromised immunity. As a result of the inhibition achieved via implementation of the disclosed embodiments, mortality and morbidity rates may be reduced, even though the number of animals treated for a respiratory condition may also be decreased.

As used herein, an "effective amount" refers to an amount capable of providing bioavailable levels of the active components sufficient to inhibit a respiratory condition. The active components included in a disclosed feed product can include one or more DFMs, one or more phytogenic compounds, and/or one or more vitamins.

The terms "base feed," "total feed," "starter feed," and "complete feed" may be used interchangeably herein. Such terms encompass feeds into which the disclosed feed products may be admixed in certain embodiments. Examples of the aforementioned feeds may be provided concurrently with one or more additional feeds or milk replacers, or feeds that provide all or a majority of the targeted animals' nutrition, e.g., complete feeds.

The term "base liquid" encompasses a variety of liquids with which the disclosed feed products can be mixed. Non-limiting examples of base liquids can include drinking water, drenches, liquid milk replacers, or milk products comprised of natural and/or supplemental milk components.

Feed Products Formulated to Inhibit Respiratory Conditions

Embodiments of the disclosed feed products may include at least one DFM, at least one phytogenic compound, and/or at least one vitamin, which may be collectively referred to as the "active components" constituting all or a portion of a given feed product. The feed products can comprise stand-alone products, supplements, or "packs." Additionally or alternatively, the feed products can be formulated for inclusion or admixing with a base feed or feed ingredients, drinking water, feed gel, and/or milk replacers before or after aqueous reconstitution. Accordingly, the feed products disclosed herein may be formed into or obtained as a supplement, additive, premix, or integral component of a base feed, complete feed, liquid, and/or gel.

As a supplement or pack, the feed products may be provided to animals separately from or together with other feeds, feed ingredients, or liquids. As an additive, the feed products may be included within or admixed with a base feed, which may constitute a complete feed or a starter feed, such that the feed products each constitute a subcomponent of a broader feed composition. As a premix, the feed products may be combined with one or more additional vitamins, minerals, or additives, and the resulting composition may be formulated for admixing with a base feed or liquid. Feed products intended for admixing with a liquid or gel may be formulated differently than feed products intended for inclusion within a dry or substantially dry base feed. For example, such feed products may be water-soluble. Additives or premixes may be formulated for combining with a feed or liquid composition at or before the time of feeding. The feed products may provide little to no nutritional benefit beyond the inhibition of a respiratory condition, such that the base feed or liquid into which the feed products are added may provide the majority or sole source of nutrients to the target animals. Alternatively, embodiments of the disclosed feed products may provide one or more benefits beyond the inhibition of a respiratory condition, such as an improvement in the overall health or performance of an animal that ingests the feed products. The physical form of the feed products may vary and may depend on whether they are utilized as a supplement, additive, or premix. Embodiments may include a dry feed product, e.g., a powder or granular composition.

The DFM(s) included in the disclosed feed products may exhibit robust production of various enzymes (e.g., amylase, lipase, proteinase, cellulase), strong pathogen inhibition, and are safe for inclusion in animal feeds. A single DFM or a blend of two or more DFMs may be included in the feed products and may be referred to as a "DFM composition" regardless of the number of unique strains included therein. For example, each feed product can include a DFM composition comprised of one or more strains of *Bacillus*, such as *B. pumilus, B. subtilis*, and/or *B. amyloliquefaciens*. Embodiments are not limited to strains of *Bacillus*, however, and may include additional bacterial strains in the same or different genus. Specific embodiments can include two strains of *B. pumilus* or a combination of *B. amyloliquefaciens* and *B. subtilis*.

In embodiments featuring two or more bacterial strains, the ratio between them may vary. For example, embodiments may feature approximately equal amounts or concentrations of two or more distinct strains of bacteria. Alternative embodiments may feature two or more strains present at a ratio of about 1:2, 2:3, 1:3, 1:4. 1:5, 1:6, 1:7, 1:8, 1:9, 1:10, or any ratio therebetween. The absolute and relative amounts of the DFM composition may vary within different embodiments of the disclosed feed products. For example, a feed product can include a DFM composition at a content of about 40 wt %, about 45 wt %, about 50 wt %, about 55 wt %, about 60 wt %, about 65 wt %, about 70 wt %, about 75 wt %, about 80 wt %, or any value therebetween. Embodiments of the feed products may also include a DFM composition at a content ranging from about 45 wt % to about 80 wt %, about 45 wt % to about 55 wt %, about 48 wt % to about 52 wt %, about 70 wt % to about 80 wt %, about 72 wt % to about 78 wt %, about 74 wt % to about 76 wt %, or any value therebetween based on the weight of the feed product. Certain embodiments may include a feed product comprised of at least 50 wt % of a DFM composition.

Direct-fed microbial compositions disclosed herein include pure or substantially pure bacterial isolates, which may include preexisting isolates, novel isolates, or novel isolate combinations discovered during the development of the feed products disclosed herein. The concentration of pure or substantially pure DFMs within a given DFM composition may vary. In embodiments, the pure or substantially pure DFMs constitute the primary component by dry weight percentage of the DFM composition, such that the pure or substantially pure DFMs constitute at least about 50 wt %, about 55 wt %, about 60 wt %, about 65 wt %, about 70 wt %, about 75 wt %, about 80 wt %, about 85 wt %, about 90 wt %, about 95 wt %, about 98 wt %, about 99 wt %, or about 100 wt % of the DFM composition.

The DFM compositions can be provided in media-free form. Metabolites of one or more bacterial strains included in a DFM composition may also be utilized, as can mixtures of live bacteria and their metabolites and/or fermentate. Non-limiting examples of such metabolites can include one or more lipopeptides and/or bacteriocins. Mutant and/or transformed strains of the bacteria disclosed herein may also be used. In some examples, one or more bacterial strains included in a feed product may originate from swine, thereby facilitating colonization of the bacteria in pigs. This feature may be directed to embodiments targeting swine because colonization can enhance the long-term benefits of the strains to the targeted hosts.

Pursuant to the development of the embodiments disclosed herein, the bacterial strains were first characterized in vitro for their probiotic and antagonistic properties related to pathogen inhibition, antibiotic resistance gene abundance, virulence factors, enzyme production, and food safety. Numerous *Bacillus*-based compositions (>65 strains) were identified and screened in successive in vitro experiments, both individually and in various combinations, against strains of *Staphylococcus* xylosus, *Streptococcus, Streptococcus suis, E. coli, Listeria innocua, Bordetella petrii, Bordetella bronchiseptica, Pseudomonas fluorescens*, and *Salmonella enterica* Cholerasuis. Screening methods included agar-well diffusion and competitive exclusion assays. Through this approach, a particular two-strain combination of *Bacillus pumilus* was identified as a particularly effective inhibitor of pathogenic bacteria and respiratory pathogens in particular. The discovery that two strains of bacteria exhibited notably antibacterial properties, despite the strains being derived from the same bacterial species, was surprising. A second two-strain blend, this time comprising a strain of *B. amyloliquefaciens* and a strain of *Bacillus subtilis*, was also discovered as an effective antibacterial composition. In view of these discoveries, the combinations of *Bacillus* identified herein may, in at least some examples, be used in one or more combinations for effective inhibition of bacterial pathogens relative to other bacterial compositions containing different or additional types of bacteria, including other species, combinations, or concentrations of *Bacillus*.

In some examples, the feed products disclosed herein may inhibit one or more of the aforementioned bacterial pathogens, e.g., *Streptococcus*, in animals provided feed or animal feed ingredients containing the feed products. As a result, animals fed the animal feed or animal feed ingredients may be shielded from the contraction of respiratory conditions caused by such bacteria, thereby reducing the animals' likelihood of developing symptoms of respiratory stress. The inhibition of pathogenic bacteria may be especially significant in group feed settings, e.g., in a feedlot or enclosed facility, where animals are more likely to spread pathogenic bacteria through communal feed rations, e.g., rations provided in shared feed troughs, feeders, or other containers. Infected animals may expose the feed to pathogenic bacteria by coughing, breathing, or otherwise contacting the feed, for example. In such scenarios, the disclosed feed products may reduce the survival of the harmful bacteria deposited on or in the feed before ingestion by one or more additional, non-infected animals.

The active components of the disclosed feed products, i.e., the DFM(s), phytogenic compound(s), and/or vitamin (s), may exert a synergistic treatment effect when included together in various combinations. The active components may also exhibit an additive effect when included together. In some examples, it may be imperative to include one or more DFMs, phytogenic compounds, and vitamins in a feed product to effectively inhibit a respiratory condition or associated symptom. In other examples, only a subset of the active components, i.e., one or more DFM(s), one or more phytogenic compound(s), or one or more vitamins, may be sufficient to effectively inhibit a respiratory condition or associated symptom. According to such examples, one or more of the active components may provide an ancillary health benefit to the target animals. Ancillary health benefits may not be directly related to respiratory treatment, but may improve overall animal health, thereby increasing the likelihood of effective respiratory treatment. In some embodiments, the feed product may include only a DFM composition and a phytogenic composition, without any vitamins. The vitamins may thus be optional according to certain implementations.

The phytogenic compound(s) included in the feed products disclosed herein may be of plant origin, e.g., plant-derived substances, products, extracts, and/or oils. The specific components of the phytogenic composition may vary and may be adjusted depending on several factors, including the respiratory health of the target animals. In embodiments, a phytogenic composition may include one or more active components or substances. In various embodiments, non-limiting examples of the active components or substances of the phytogenic composition may include quillaja extract (e.g., *Quillaja saponaria*), one or more citrus bitter extract flavonoids (e.g., *Citrus aurantium*), curcuma extract (e.g., *Curcuma longa*), *Capsicum annuum*, and/or at least one essential oil such as thymol and/or eugenol. Embodiments may include cayenne pepper derived from the *Capsicum annuum* species of peppers. One or more of the aforementioned phytogenic compounds, additional species of which may be acceptable, can be included in the feed products in powdered form. In some implementations, the phytogenic composition may include two or more or the aforementioned phytogenic compounds.

The absolute and relative amounts of each phytogenic component may vary within embodiments of the disclosed feed products. For example, feed products can have a quillaja extract content ranging from about 0 wt % to about 25 wt %, about 2 wt % to about 20 wt %, about 4 wt % to about 15 wt %, about 6 wt % to about 13 wt %, about 8 wt % to about 11 wt %, about 9 wt %, about 10 wt %, or any value therebetween based on the weight of the feed product. Feed product embodiments can have a *Citrus aurantium* content ranging from about 0 wt % to about 25 wt %, about 2 wt % to about 20 wt %, about 4 wt % to about 15 wt %, about 6 wt % to about 13 wt %, about 8 wt % to about 11 wt %, about 9 wt %, about 10 wt %, or any value therebetween based on the weight of the feed product. Embodiments can have a combined *Curcuma longa* and *Capsicum annuum* content ranging from about 3 wt % to about 32 wt %, about 5 wt % to about 30 wt %, about 7 wt % to about 27 wt %, about 9 wt % to about 24 wt %, about 11 wt % to about 21 wt %, about 13 wt % to about 18 wt %, about 15 wt % to about 17 wt %, about 16 wt %, or any value therebetween based on the weight of the feed product. In some examples, the curcuminoid content, which may be comprised in whole or in part of *Curcuma longa* and/or curcumin derivatives, may be at least 3 wt %, at least 4 wt %, at least 5 wt %, or more. Examples can include a blend of at least two essential oils, which may comprise thymol and/or eugenol. Embodiments featuring a blend of both thymol and eugenol can be included at a content ranging from about 1 wt % to about 16 wt %, about 1 wt % to about 14 wt %, about 2 wt % to about 13 wt %, about 3 wt % to about 12 wt %, about 4 wt % to about 11 wt %, about 5 wt % to about 10 wt %, about 6 wt % to about 9 wt %, about 7 wt % to about 8 wt %, or any value therebetween based on the weight of the feed product. In some examples, thymol can be included at a content ranging from about 3 wt % to about 15 wt %, about 4 wt % to about 12 wt %, about 5 wt % to about 10 wt %, about 6 wt % to about 8 wt %, or any value therebetween based on the weight of the feed product. In some examples, eugenol can be included at a content ranging from about 0.1 wt % to about 10 wt %, about 0.5 wt % to about 8 wt %, about 1 wt % to about 6 wt %, about 1 wt % to about 5 wt %, about 2 wt % to about 4 wt %, or any value therebetween based on the weight of the feed product. Accordingly, in embodiments of the feed product containing both thymol and eugenol, the thymol:eugenol ratio may range from about 1:1 to about 10:1. In some embodiments, the phytogenics may be present at a 1:1 ratio, and for instance *Citrus aurantium* may be present at a 1:1 ratio with an essential oil or a blend thereof as disclosed herein. In other embodiments, the phytogenics may be present at a ratio of about 1:2, 1:1, 3:5, or 4:5, and for instance *Curcuma longa* and *capsicum* annum in combination with the *Quillaja saponaria* may be present at a ratio of 3:5.

In some embodiments, the phytogenic composition may be free of one or more of the aforementioned active components. In embodiments where one or more components of the phytogenic composition listed above are omitted, the amounts of the remaining components may be increased accordingly, provided that no additional active components replace the omitted component. For example, if one or more active phytogenic components are omitted, the remaining components of the feed product may be increased.

Each feed product can contain one or more vitamins, which can supplement the vitamins already present in the composition(s) with which the feed product is mixed, non-limiting examples of which may include premixes containing a combination of vitamins and minerals. A single vitamin or blend of two or more vitamins can be included, non-limiting examples of which may include forms of vitamin C and/or vitamin D. Specific vitamins can include esters of L-ascorbic acid and/or 25-hydroxyvitamin D3. Additional esters and vitamin derivatives can also be included. The absolute and relative amounts of each vitamin may vary within different embodiments of the disclosed feed products. For example, feed products can include esters of L-ascorbic acid at contents ranging from about 0 wt % to about 6 wt %, about 0.25 wt % to about 5 wt %, about 0.5 wt % to about 4 wt %, about 0.75 wt % to about 3 wt %, about 1 wt % to about 2 wt %, about 1.25 wt % to about 1.75 wt %, about 1.5 wt %, or any value therebetween based on the weight of the feed product. Embodiments can include 25-hydroxyvitamin D3 at contents ranging from about 0 wt % to about 6 wt %, about 0.25 wt % to about 5 wt %, about 0.5 wt % to about 4 wt %, about 0.75 wt % to about 3 wt %, about 1 wt % to about 2 wt %, about 1.25 wt % to about 1.75 wt %, about 1.5 wt %, or any value therebetween based on the weight of the feed product. In some embodiments, the vitamins may be present at a 1:1 ratio.

In some embodiments, the feed product may be free of one or more of the aforementioned vitamins. In embodiments where one or more vitamins are omitted, the amounts of the remaining components may be increased accordingly, provided that no additional vitamins replace the omitted component. For example, if one or more vitamins are omitted, the remaining active components may be increased.

In certain embodiments of the feed products, for example embodiments including two strains of *Bacillus pumilus*, the DFM composition can constitute about 45 wt % to about 85 wt % of the feed product, or about 50 wt %, about 55 wt %, about 60 wt %, about 65 wt %, about 70 wt %, about 75 wt %, about 80 wt %, or any value therebetween. According to the same embodiments, the phytogenic composition can constitute about 5 wt % to about 35 wt % of the feed product, or about 10 wt %, about 15 wt %, about 20 wt %, about 25 wt %, about 35 wt %, or any value therebetween. The same embodiments can include a vitamin content ranging from about 5 wt % to about 30 wt % of the feed product, or about 10 wt %, about 15 wt %, about 20 wt %, about 25 wt %, or any value therebetween.

In additional embodiments of the feed products, for example embodiments including one or more strains of *B. amyloliquefaciens* and *B. subtilis*, the DFM composition can constitute about 40 wt % to about 60 wt % of the feed product, or about 45 wt %, about 50 wt %, about 55 wt %, or any value therebetween. According to the same embodiments, the phytogenic composition can constitute about 5 wt % to about 20 wt % of the feed product, or about 7 wt %, about 9 wt %, about 11 wt %, about 13 wt %, about 15 wt %, about 17 wt %, about 19 wt %, or any value therebetween. The same embodiments can include a vitamin content ranging from about 5 wt % to about 35 wt % of the feed product, or about 10 wt %, about 15 wt %, about 20 wt %, about 25 wt %, about 35 wt %, or any value therebetween.

In some embodiments, the feed products may comprise one or more additional agents configured to preserve or protect the active components, enhance the effectiveness of the active components after ingestion, formulate the active components for a specifically timed release, and/or improve the palatability of the active components to the target animals. In some embodiments, the additional agents may include one or more carrier components formulated to protect the active components from immediate degradation. In addition or alternatively, the carrier component(s) may facilitate targeted digestion of the active components. The carrier components may be provided as a coating around the active components, or may be integrally mixed with the active components. In some examples, the carrier components may include wheat bran and/or calcium carbonate. Non-limiting examples of additional agents may include anti-caking agents, flavorants, desiccants, emulsifiers, preservatives, stabilizers, protective coatings, salts, and combinations thereof. The agents may be food-safe for the selected animal. The absolute and relative amounts of each additional agent may vary in different embodiments.

In some examples, the feed products may be partially or wholly encapsulated or coated for controlled release of one or more active components contained therein. Encapsulation may protect a given feed product from early degradation in animals after ingestion. Early degradation may be defined as degradation and/or digestion upstream of the stage of digestion optimal for nutrient absorption into the animals' bloodstream. Accordingly, the timing and location of early degradation likely varies in different animals. For example, encapsulation may protect the feed product from early degradation in the rumen of ruminants. The encapsulant may be pH-activated in some embodiments, such that the encapsulant is formulated to decompose and release the active component(s) in an environment having a specific pH, e.g., the small intestine. In some embodiments, the encapsulant comprise at least one microbial cell wall-based component. In addition or alternatively, the encapsulant may contain one or more fat- or wax-based components, e.g., fatty acid glycerides, formulated to protect the active component(s) from early degradation, thereby preserving them for maximum absorption. Acceptable examples of fat-based encapsulants are described in U.S. Pat. No. 9,986,749 to Boucher et al., the entire contents of which are incorporated by reference herein. In some examples, the encapsulant may comprise lipid-based nanoparticles (about 200-500 nm in diameter).

The disclosed feed products may be admixed or otherwise combined with a base feed, e.g., a complete feed, feed ingredients, and/or starter feed, in an amount effective to inhibit a respiratory condition in animals fed the resulting mixture. The form of the base feed may vary. For example, the base feed may be provided as a pellet, meal, or crumble. The base feed may provide the basic nutritional and bulk feed components needed in the diet of the animals. In some examples, the base feed may be the primary food source, by weight, of the animals' diet, which may be supplemented by other natural food sources, e.g., forages. In embodiments, the physical form and/or composition of the base feed may vary. For example, the base feed may be provided as a pellet of variable size, e.g., 3/32" or 11/64". In other embodiments, the base feed may include extruded nuggets, granular mixtures, feed blocks, mineral blocks, feed tubs, paste compositions, gels, and/or combinations thereof. Accordingly, the texture and moisture level of the base feed may also vary.

Embodiments of the base feed disclosed herein can comprise a complete animal feed, which may be a grain-based feed formulated specifically for swine, cattle, or poultry. At least a portion of the base feed may comprise corn or corn-based products, wheat or wheat-based products, soybeans or soybean-based products, poultry byproducts, grain sorghum, barley, or combinations thereof. Non-limiting example components of acceptable base feeds can include one or more of: ground corn, sugar, dehulled soymeal, soy isolate, hydrolyzed soy protein, dried distillers grains with solubles, poultry byproduct meal, or any combination thereof, along with various vitamins, minerals, and/or additives, non-limiting examples of which may include: calcium carbonate, choline chloride, lysine, methionine, selenium, threonine, tryptophan, valine, zinc oxide, lactose source, salt, selenium yeast, and/or intake enhancing product.

The nutrient profile of the base feed generally includes various amounts of crude protein, crude fat, crude fiber, carbohydrates, and assorted vitamins and minerals, each combined in various amounts to produce a feed having variable dry matter and moisture content. This disclosure is not limited to any particular nutrient profile, such that the disclosed feed products can be admixed or otherwise combined with base feeds having various amounts of protein, fat, fiber, carbohydrates, sugar, etc. The total protein content of the base feed may be about 14 wt %, about 15 wt %, about 16 wt %, about 17 wt %, about 18 wt %, about 19 wt %, about 20 wt %, about 21 wt %, about 22 wt %, about 23 wt %, about 24 wt %, or more, or any level of protein therebetween. Embodiments of the base feed may contain crude fat at a level ranging from about 1 wt % to about 10 wt %, for example about 2 wt %, about 3 wt %, about 4 wt %, about 5 wt %, about 6 wt %, about 7 wt %, about 8 wt %, or any level therebetween. Embodiments of the base feed may contain fiber at a level ranging from about 1 wt % to about 10 wt %, for example about 2 wt %, about 3 wt %, about 4 wt %, about 5 wt %, about 6 wt %, about 7 wt %, about 8 wt %, about 9 wt %, or any level therebetween. Embodiments of the base feed may contain one or more amino acids, e.g., lysine, at a level ranging from about 0.1 wt % to about 2 wt %, for example about 0.2 wt %, about 0.3 wt %, about 0.4 wt %, about 0.5 wt %, about 0.6 wt %, about 0.7 wt %, about 0.8 wt %, about 0.9 wt %, about 1 wt %, about 1.1 wt %, about 1.2 wt %, about 1.3 wt %, about 1.4 wt %, about 1.5 wt %, about 1.6 wt %, about 1.7 wt %, about 1.8 wt %, about 1.9 wt %, or any level therebetween. Additional vitamins and minerals, such as monocalcium phosphate, dicalcium phosphate, calcium carbonate, sodium carbonate, sodium bicarbonate, sodium chloride, potassium chloride, potassium carbonate, potassium iodate, magnesium oxide, ferric oxide, ferrous oxide, calcium oxide, calcium hydroxide, chromic oxide, copper oxide, copper sulfate, zinc oxide, calcium chloride, copper sulfate, trace amounts of selenium, chromium, cobalt, molybdenum, manganese, fluoride, iodine, and the like may be present at various levels.

After combining the feed product with a base feed, the resulting product may be dry or substantially dry, such that moisture level is zero, or close to zero. In some examples, moisture may be present in the base feed at less than about 5 wt %, such as about 0.1 wt %, about 0.2 wt %, about 0.3 wt %, about 0.4 wt %, about 0.5 wt %, about 0.6 wt %, about 0.7 wt %, about 0.8 wt %, about 0.9 wt %, about 1 wt %, about 1.5 wt %, about 2 wt %, about 2.5 wt %, about 3 wt %, about 3.5 wt %, about 4 wt %, about 4.5 wt %, or any level therebetween.

After admixing with a base feed, the disclosed feed products can constitute various levels of the resulting mixture. The feed products, each containing a DFM composition, a phytogenic composition, and optionally at least one vitamin, may be present within a feed mixture at levels ranging from about 0.01 wt % to about 0.5 wt %, including but not limited to about 0.02 wt %, about 0.03 wt %, about 0.04 wt %, about 0.05 wt %, about 0.06 wt %, about 0.07 wt %, about 0.08 wt %, about 0.09 wt %, about 0.1 wt %, about 0.2 wt %, about 0.3 wt %, or about 0.4 wt % of the total feed product.

In embodiments, the phytogenic compounds and/or vitamins of the feed products may be included in a base feed at inclusion rates ranging from less than about 20 g/ton to about 20 g/ton, about 20 g/ton to about 500 g/ton, greater than 500 g/ton, or any concentration therebetween, such as about 40 g/ton, about 50 g/ton, about 60 g/ton, about 70 g/ton, about 80 g/ton, about 90 g/ton, about 100 g/ton, about 110 g/ton, about 120 g/ton, about 130 g/ton, about 140 g/ton, about 150 g/ton, about 160 g/ton, about 170 g/ton, about 180 g/ton, about 190 g/ton, about 200 g/ton, about 210 g/ton, about 220 g/ton, about 230 g/ton, about 240 g/ton, about 250 g/ton, about 260 g/ton, about 270 g/ton, about 280 g/ton, about 290 g/ton, about 300 g/ton, about 310 g/ton, about 320 g/ton, about 330 g/ton, about 340 g/ton, about 350 g/ton, about 360 g/ton, about 370 g/ton, about 380 g/ton, about 390 g/ton, about 400 g/ton, about 410 g/ton, about 420 g/ton, about 430 g/ton, about 440 g/ton, about 450 g/ton, about 460 g/ton, about 470 g/ton, about 480 g/ton, or about 490 g/ton.

In embodiments, the DFM compositions of the feed products may be included in a base feed at inclusion rates ranging from less than about 50,000 CFUs/gram to about 100,000 CFUs/gram, to about 200,000 CFUs/gram, to about 300,000 CFUs/gram, to about 400,000 CFUs/gram, to about 500,000 CFUs/gram, to about 600,000 CFUs/gram, to about 700,000 CFUs/gram, to about 800,000 CFUs/gram, to about 900,000 CFUs/gram, to about 1 million CFUs/gram, to about 10 million CFUs/gram, to about 20 million CFUs/gram, to about 30 million CFUs/gram, to about 40 million CFUs/gram, to about 50 million CFUs/gram, to about 60 million CFUs/gram, to about 70 million CFUs/gram, to about 80 million CFUs/gram, to about 90 million CFUs/gram, to about 100 million CFUs/gram, from about 100 million CFUs/gram to about 400 million CFUs/gram, greater than 400 million CFUs/gram, or any concentration therebetween, such as about 120 million CFUs/gram, about 140 million CFUs/gram, about 160 million CFUs/gram, about 180 million CFUs/gram, about 200 million CFUs/gram, about 220 million CFUs/gram, about 240 million CFUs/gram, about 260 million CFUs/gram, about 280 million CFUs/gram, about 300 million CFUs/gram, about 320 million CFUs/gram, about 340 million CFUs/gram, about 360 million CFUs/gram, or about 380 million CFUs/gram.

In some examples, the feed products may be formulated for admixing with a base liquid, such as water or milk replacer, in an amount effective to inhibit a respiratory condition in animals fed the resulting solution, suspension or mixture, either alone or in combination with a feed composition supplemented with the feed products. The components and nutritional profiles of such liquids may vary, and may depend on the targeted animals. For example, a calf milk replacer can be milk and/or vegetable based, and the nutrient profile generally includes fat and protein.

The fat content of the milk replacers into which the feed products are mixed may range from about 2.25 wt % to about 4.7 wt % of the hydrated milk replacer or from about 8 wt % to about 31 wt % of the milk replacer powder. The level of fat may be tailored for a target animal, e.g., calves, as well as the age of the animals fed. In some examples, a calf milk replacer may include a crude fat content ranging from about 10 wt % to about 20 wt % of the powder or about 3 wt % to about 3.75 wt % of the hydrated milk replacer, and full potential calf milk replacers may include fat from about 25 wt % to about 31 wt % of the powder or about 3.75 wt % to about 4.7 wt % of the hydrated milk replacer. In some embodiments, the powdered milk replacer may have a crude fat content of about 8 wt % to about 12 wt %, about 9 wt % to about 11 wt %, about 10 wt %, about 14 wt % to about 20 wt %, about 16 wt % to about 18 wt %, or about 17 wt %.

Protein in milk replacers typically ranges from about 2.2 wt % to about 5.1 wt % of the hydrated milk replacer or about 18 wt % to about 30 wt % of the powder. For traditional calf milk replacers, the protein content may be about 22 wt % of the powder or about 3.3 wt % of the rehydrated milk replacer, and milk replacers formulated for enhanced performance, such as full potential milk replacers, may include protein at about 25 wt % to about 28 wt % of the powder or about 3.9 wt % to about 4.8 wt % of the rehydrated milk replacer. Protein may be sourced from animal (e.g., milk, plasma, egg, and red blood cells) and vegetable sources and combinations thereof. Milk-derived protein sources are generally referred to as milk proteins and may include whey, casein, skim milk, sodium caseinate, and calcium caseinate. Non-milk proteins (NMPs), such as vegetable protein (e.g., soy protein, hydrolyzed soy protein, hydrolyzed soy protein modified, soy protein isolate, wheat concentrates, wheat isolates, pea concentrates, pea isolates, and/or potato proteins), animal protein (e.g., plasma such as bovine or porcine plasma, egg and red blood cells), and single cell protein, alone or in combination, may be included as a protein source in the milk replacer.

In some embodiments, a disclosed feed product can be offered concurrently with or in addition to one or more antibiotics or medicinal compounds. In such embodiments, the feed product and the antibiotic(s) can provide a synergistic or additive effect with respect to respiratory condition inhibition, thereby reducing, eliminating or preventing symptoms of the condition to a greater extent than either the feed product or the antibiotic(s), alone. The amount of antibiotics used in combination with the feed products may be reduced relative to approaches where antibiotics are used without the feed products of the present disclosure. Examples may also exclude one or more antibiotics, and may be antibiotic-free.

Methods of Inhibiting Respiratory Conditions

Methods of inhibiting respiratory conditions in animals involve feeding the animals an effective amount of a feed product disclosed herein, either as a stand-alone product or as a component of a base feed or liquid. Non-limiting examples of particular animals fed the disclosed feed products can include various breeds of swine, ruminants, poultry, or companion animals. The animals may have observable respiratory distress or be diagnosed with a respiratory condition, exhibiting symptoms of a respiratory condition, or at risk of contracting a respiratory condition, although methods may also be applied to healthy animals that may not be at a notable risk of contracting a respiratory condition.

Methods may involve initially forming a feed product or simply obtaining it, for example via purchase. As noted above, embodiments may involve combining the feed product with a base feed or liquid at or prior to feeding. Pursuant to such embodiments, an animal producer may purchase, produce or otherwise obtain a base feed lacking a feed product disclosed herein. Examples can involve admixing the feed product with the base feed on a routine or semi-routine basis, for example once per day, and subsequently offering the resulting mixture to the target animals, for example on the day of mixing or the day after mixing. Embodiments may also involve admixing the feed product with a base feed and placing the resulting mixture in a self-feeder, which may be configured to supply the target animals with adequate amounts of feed for one or more days or weeks at a time, thereby necessitating less frequent admixing of the feed product with the base feed. The feed product can be admixed with the base feed in any convenient manner that ensures the feed product is ultimately ingested by the target animals. For example, the feed product may be admixed with feed components during production of a feed mixture, such as a feed supplement or a premix. The feed product may additionally or alternatively be top-dressed over a base feed or feed components, such top-dressing over feed contained within a feeding trough or deposited on a flat surface. In some embodiments, the base feed may contain a disclosed feed product, such that the animal producer may simply obtain the final feed product and then provide it directly to the animals. The feed product can be fed in any form which is suitable for feeding the animals.

In some examples, the base feeds/liquids and the feed product may be provided to end users in separate containers or packages. In such embodiments, the user may be instructed to admix the feed product with the base feed and/or liquid according to one or more instructions provided on the packaging for the feed product. Instructions may indicate acceptable amounts of feed product to be admixed with various amounts of feed and/or liquid. Instructions may also provide methods of adjusting the concentration of the feed product within the base feed and/or liquid in response to variations in the severity of respiratory stress exhibited by the animals. The instructions may also indicate acceptable time frames to begin feeding animals in anticipation of conditions conducive to respiratory stress. In some embodiments, the instructions may include one or more warning signs, e.g., symptoms of respiratory stress, prompting end users to begin mixing the feed product with the base feed or liquid and providing the resulting composition to the animals.

According to certain implementations of use, a disclosed feed product may be provided in the diet of the animal during all or a portion of the year in which the animal is or may be challenged by respiratory-associated issues (e.g., based on historical seasonal patterns of respiratory sickness) to improve animal performance during such periods of stress. For instance, the feed product may be provided during the seasonal changes, such as fall to winter, and winter to spring, or during the winter months. The feed product may also be provided intermittently during the year in anticipation of periods of respiratory-associated issues (e.g., where an animal is housed with other animals showing signs or symptoms of respiratory-associated issues), and for instance the animal may be prophylactically provided the product.

In another implementation, the feed product may be included in the diet of the animal only during periods of observed respiratory-associated issues in the animal. Respiratory-associated issues may include but are not limited to infections affecting the lungs of the animal, for instance caused by pathogens responsible for respiratory-associated diseases including *Streptococcus, Staphylococcus, Bordetella, Pasteurella*, and other pathogens, respiratory stress, increased respiration from about 45-75 cycles per minute standing, or about 40-70 cycles per minute recumbent, panting, shallow breathing, coughing and combinations of such respiratory-associated issues. Respiratory-associated issues may also decrease animal performance (e.g., decrease rate of weight gain, increase weight loss, and decrease feed or fluid intake (e.g., reductions of about 5%, 10%, 15%, 20%, or more)), and/or increase other symptoms such as elevated internal body temperature, open mouth breathing, excessive panting, sweating, lethargy, shakiness, thumping, back end weakness, increased spine curvature, lameness, and failed reproduction may also be attributed to respiratory-associated issues experienced by the animal, for example those caused by *Streptococcus* infections. Three different presentations of *Streptococcus* may appear: (1) peracute, (2) acute, and (3) chronic. The peracute form may not present any clinical signs; the animals may simply be found dead without warning. For the acute form, an initial symptom may be fever and associated anorexia and depressed behavior. Affected animals often present signs of meningitis, such as squinting eyes and flattened ears. Depression, paddling, ataxia, nystagmus, and head tilts are also common, especially for infections caused by *Streptococcus suis*. Polyarthritis is a common symptom of the chronic form and is frequently accompanied by swollen joints and lameness. *Streptococcus suis* may cause or contribute to cases of pneumonia, and/or may be a secondary and opportunistic pathogenic bacteria associated with the condition.

The amount of the feed product ingested per animal may vary and may depend on a numerous factors, non-limiting examples of which include the starting concentration of one or more components of the feed product, the number of feedings administered per day, the specific breed or species of the target animal, the age and/or size of the target animal, the life stage of the target animal, the concentration of the feed product within the final feed or liquid composition, and/or whether the target animal has been diagnosed with or is exhibiting symptoms of a respiratory condition. In some embodiments, animals may be fed less than or about 0.25 grams of the feed product per head per day, or about 0.25 grams to about 10 grams per head per day, more than 10 grams per day or any value therebetween, such as 0.5 grams, 1.0 grams, 1.5 grams, 2.0 grams, 2.5 grams, 3.0 grams, 3.5 grams, 4.0 grams, 4.5 grams, 5.0 grams, 5.5 grams, 6.0 grams, 6.5 grams, 7.0 grams, 7.5 grams, 8.0 grams, 8.5 grams, or 9.5 grams per head per day.

Embodiments may involve feeding the animals a disclosed feed product on an ad libitum basis throughout a feeding period. An ad libitum basis as contemplated herein means that feed product is placed in a feeder or on a suitable surface (for example within a broader feed or liquid composition) and the animal consumes it until satisfied, such that the feed products described herein are always available to the animal for consumption at free will. In additional embodiments, one or more animals may be fed according to a more controlled feeding regimen, such that one or more defined rations are offered one or more times per day, e.g., once daily, twice daily or three times daily. The particular manner in which a feed product is fed to the animals is not intended to be limited. Any manner suitable for feeding animals may be satisfactory.

The amount of base feed or liquid ingested per animal per day can vary, and may depend largely on the age and breed of the animal. Swine ingesting a pelleted feed composition containing the feed product, for example, may ingest about 0.1 lbs. to about 10 lbs. per day, about 0.5 lbs. to about 8 lbs. per day, about 1.0 lbs. to about 6 lbs. per day, about 2 lbs. to about 4 lbs. per day, greater than 10 lbs. per day, or any amount therebetween. The embodiments disclosed herein are not limited to any particular daily consumption rate.

The duration of the feeding method may also vary, for example ranging from less than or about 1 week, about 2 weeks, about 3 weeks, 4 weeks, about 5 weeks, about 6 weeks, about 7 weeks, about 8 weeks, about 9 weeks, about 10 weeks, or longer, or any length therebetween. The disclosed feed products may be fed to animals of any age for any length of time. For example, a particular base feed may be supplemented with a disclosed feed product for as long as the base feed is typically provided to the animals. The animals may be fed the feed or liquid compositions containing the feed product on a consistent basis, e.g., daily, at least until respiratory stress conditions and/or symptoms subside. In some embodiments, one or more animals may be fed the feed compositions for a period of time after the disappearance of respiratory stress indicators to prevent a reemergence of one or more respiratory conditions. The target animals can be fed the feed products before, during, and/or after weaning, e.g., during at least a portion of the grower and/or post-grower phase, and may be admixed with different feed or liquid compositions as a result. For example, calves may ingest the feed products via a liquid milk replacer before, during, and/or after weaning, after which the calves may ingest the feed products via a dry or substantially dry feed composition. Pigs may ingest the feed products via a pelleted feed and/or meal composition before, during, and/or after weaning, including, for example, during and/or after the growing phase. The animals may be variously sized during the feeding period(s). For example, swine offered the disclosed feed products may range from about 10 pounds to about 200 pounds or more, or any weight therebetween.

The amount or concentration of the feed products provided to the animals can remain substantially constant or change over time, for example such that the daily feeding rate and/or inclusion rate may be different for unweaned or recently weaned animals, e.g., swine, relative to partially- or fully-grown animals, e.g., swine in the growing or finishing phase.

The disclosed embodiments are not limited to one mechanism or theory of inhibition; however, feeding the disclosed feed products to animals can trigger the gut-lung immune axis and improve the overall health of the animal recipients. Through competitive exclusion and the production of antimicrobial substances, the DFM compositions included in the disclosed feed products can function as probiotics configured to inhibit the growth of multiple pathogens, including gram positive and gram negative bacteria, which frequently contribute to the development of respiratory conditions. Specific embodiments may exhibit an antibacterial effect against strains of *Streptococcus, Staphylococcus, Bordetella*, and/or *Pasteurella multocida*. The feed products may also ameliorate one or more effects underlying or exacerbating a respiratory condition. For example, ingestion of the feed products may balance pro-inflammation and anti-inflammation, boost antioxidation, improve gut barrier function, improve nutrient absorption and transport, stimulate endogenous enzyme production, and/or enhance the antimicrobial quotient of the target animals' microbiome. As discussed above, the feed products disclosed herein may become active after ingestion by the target animals, for example upon reaching the animals' GI tract, where the feed products may be activated in the manner necessary to release bacteriocins specific to one or more pathogenic bacterial species or strains implicated in respiratory stress.

The methods disclosed herein may improve the performance of animals at risk of contracting, already afflicted with, or recovering from a respiratory condition. Indicators of improved performance may vary from animal to animal, and may depend on various factors including animal age and/or the severity of respiratory symptoms exhibited by the animal prior to administration of a feed product disclosed herein. In embodiments, improved performance may relate to a direct reversal of one or more respiratory stress symptoms and/or improvements to animal health not directly tied to a reduction in respiratory stress. In some examples, improved performance may encompass a reduced mortality and removal rate and/or a reduced need for respiratory treatment, for example involving injection or administration of a medication or antibiotic. The disclosed feed products may also decrease the of white blood cells to lymphocytes, which suggests that the feed products may reduce the inflammation of pigs afflicted with various health issues, including those linked to respiratory stress. Additional non-limiting examples of improved performance may include reduced feed-to-gain ratios, increased average daily weight gain, increased total weight gain over various periods of time, increased feed consumption, or combinations thereof, relative to animals fed the same base feed but lacking the feed products disclosed herein.

FIG. 1 shows an example method 100 of feeding livestock animals, which may be a pigs, ruminants, poultry, etc. As shown at step 102, the method 100 may involve feeding the livestock animals a feed composition comprising a direct-fed microbial composition and a phytogenic composition, and optionally a vitamin composition. As shown at detail 102*a*, the direct-fed microbial composition can comprise two or more strains of *Bacillus* selected from strains of *Bacillus pumilus, Bacillus subtilis*, and *Bacillus amyloliquefaciens*. As shown at detail 102*b*, the phytogenic composition can comprise one or more phytogenic compounds of: quillaja, a citrus flavonoid, curcuma, capsicum, thymol essential oil, and eugenol essential oil. As shown at detail 102*c*, the optional vitamin composition can comprise one or more forms of vitamin C and/or vitamin D.

Figure 2:
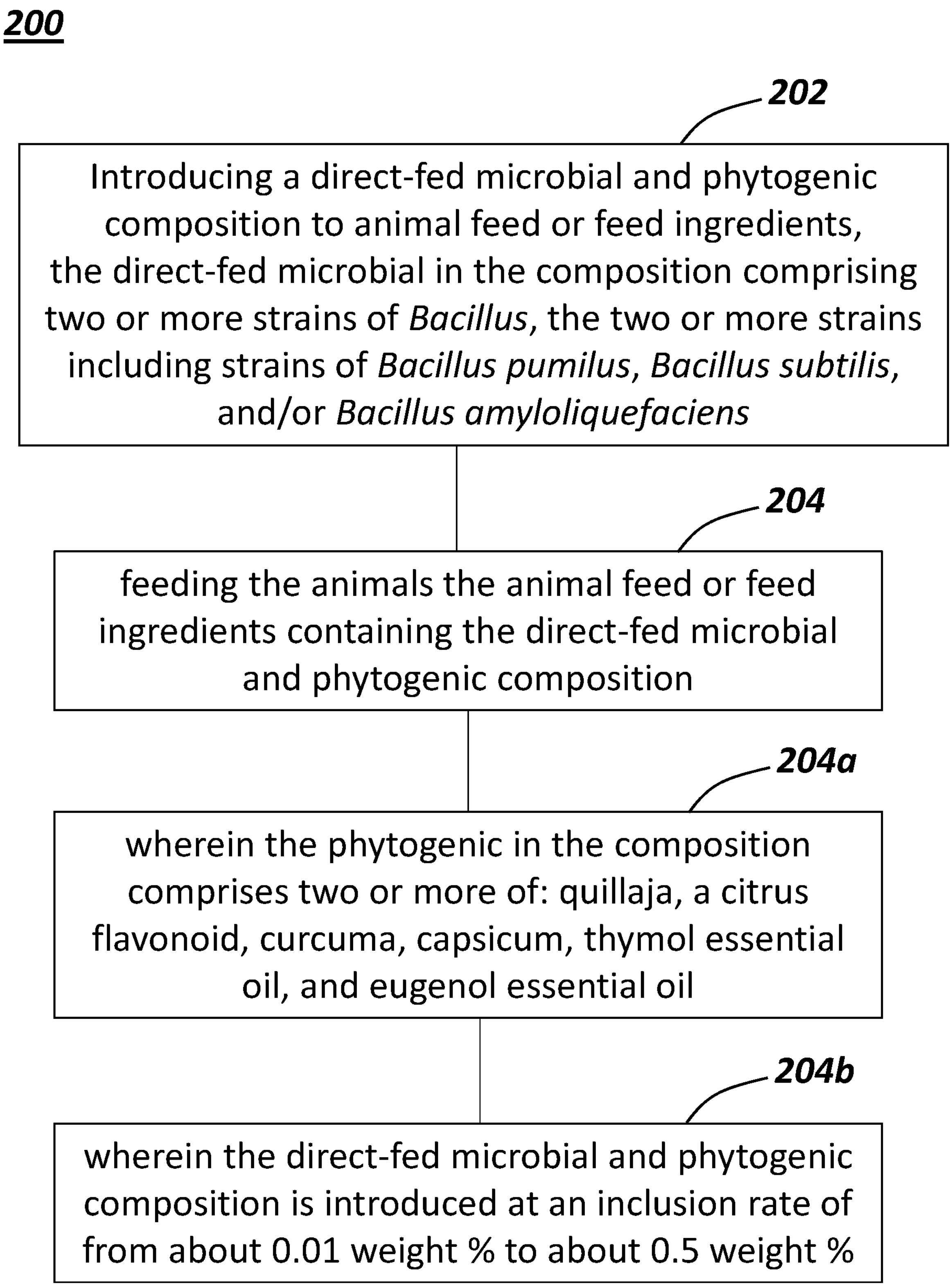
FIG. 2 is a flow chart showing a method of inhibiting *Streptococcus* in animals according to embodiments of the present disclosure.

FIG. 2 shows an example method 200 of inhibiting *Streptococcus* in animals. As shown at step 202, the method 200 may involve introducing a direct-fed microbial and phytogenic composition to animal feed or feed ingredients, the direct-fed microbial in the composition comprising two or more strains of *Bacillus*, the two or more strains including strains of *Bacillus pumilus, Bacillus subtilis*, and/or *Bacillus amyloliquefaciens*. At step 204, the method 200 may involve feeding the animals the animal feed or feed ingredients containing the direct-fed microbial and phytogenic composition. As shown at detail 204*a*, the phytogenic in the composition can comprise two or more of: quillaja, a citrus flavonoid, curcuma, capsicum, thymol essential oil, and eugenol essential oil. As shown at detail 204*b*, the direct-fed microbial and phytogenic composition can be introduced at an inclusion rate of from about 0.01 weight % to about 0.5 weight %.

Figure 3:
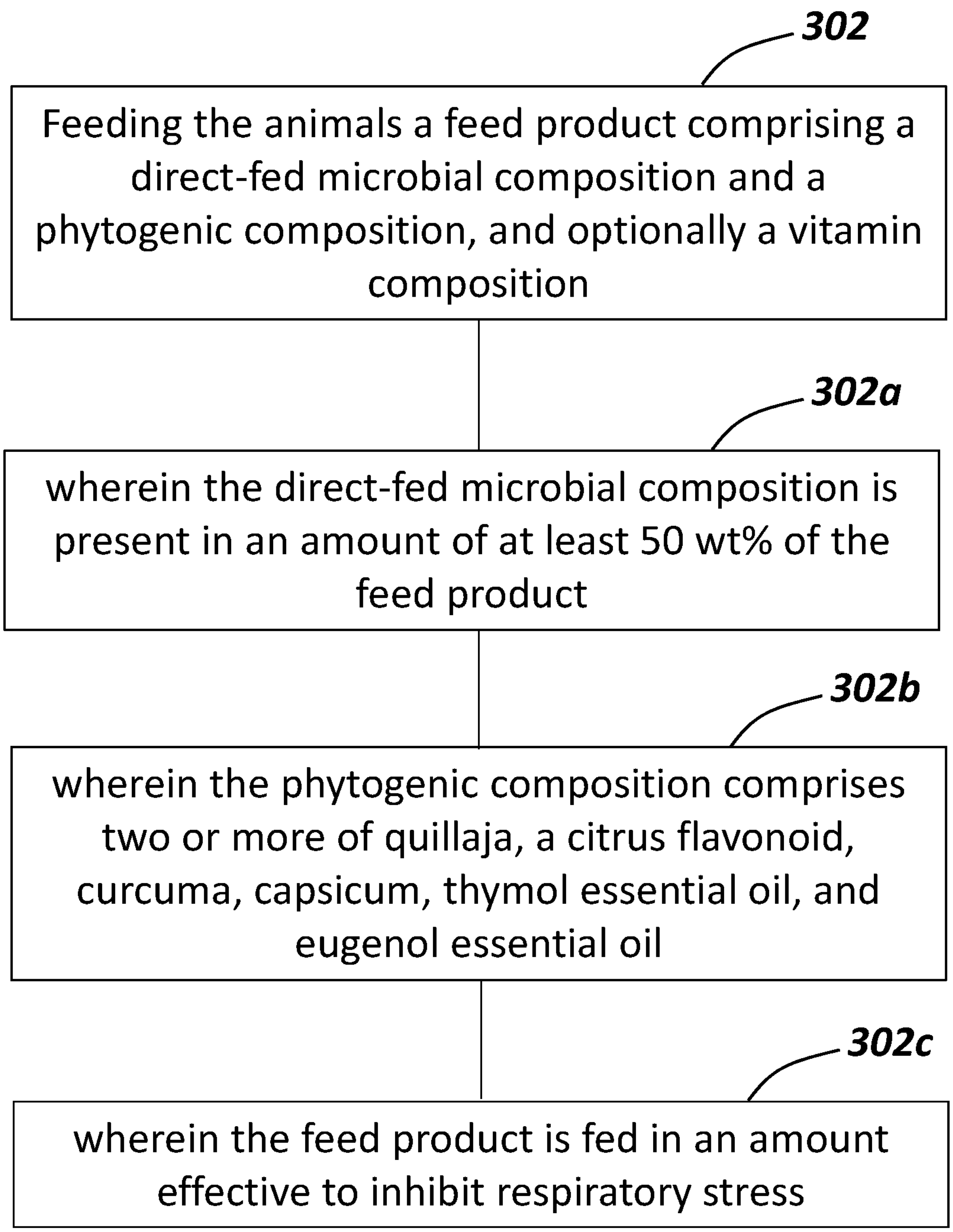
FIG. 3 is a flow chart showing a method of inhibiting respiratory stress in animals according to embodiments of the present disclosure.

FIG. 3 shows an example method of inhibiting respiratory stress in animals. As shown at step 302, the method 300 may involve feeding the animals a feed product comprising a direct-fed microbial composition and a phytogenic composition, and optionally a vitamin composition. As shown at detail 302*a*, the direct-fed microbial composition can be present in an amount of at least 50 wt % of the feed product. As shown at detail 302*b*, the phytogenic composition can comprise two or more of quillaja, a citrus flavonoid, curcuma, capsicum, thymol essential oil, and eugenol essential oil. As shown at detail 302*c*, the feed product can be fed in an amount effective to inhibit respiratory stress.

The following experimental trials are disclosed for illustrative purposes only. Numerous modifications and variations are within the scope of the present disclosure as will be apparent to those skilled in the art.

Trial 1

Trial 1 was conducted to determine whether feeding feed products comprising combinations of *Bacillus pumilus* with various phytogenic compositions and vitamins can improve the health and performance of nursery pigs. The experiment evaluated three experimental feed products or "packs," each containing a unique combination of *B. pumilus*, vitamins C and D, and phytogenic additives, on the respiratory health and growth performance of nursery pigs over a 44 day span.

Five hundred sixteen weaned pigs averaging 19 days old and weighing 14 lbs. were used in Trial 1, which was a three-phase feeding trial. At weaning, the pigs were separated by initial body weight and gender and allotted to 44 pens with 11-13 pigs per pen. Pens within each weight block were then assigned to one of four dietary treatments such that there were 11 pens per treatment.

All pigs were housed in a wean-to-finish facility with a concrete floor, five-hole metal feeder, and two nipple waterers. Room temperature was maintained at approximately 78° F. throughout the first week of the trial and then decreased by 3° F. per week thereafter. Room temperatures and humidity levels were recorded daily. Each pen was supplemented with a thermostatically controlled electrical heat mat during the first 14 days post-weaning. Pigs were allowed ad libitum access to dry feed and water throughout the study.

One of four different feed compositions was offered to each group of test animals such that each animal group was defined by the unique feed composition offered thereto. The first feed composition served as a negative control consisting of a base feed, only. The second feed composition included the same base feed but supplemented with a feed pack (pack 1) comprised of a DFM composition containing two *Bacillus pumilus* isolates ("C12") and phytogenic blend 1. The third feed composition included the base feed supplemented with feed pack 2, which included the C12 DFM composition and phytogenic blend 2. The fourth feed composition included the base feed supplemented with feed pack 3, which included the C12 DFM composition and phytogenic blend 3. Each feed composition was offered to the animals in three phases together spanning a total of 44 days. As shown below in Table 1, the first phase spanned days 0-10, the second phase spanned days 10-23, and the third phase spanned days 23-44. The feed compositions were provided in pellet form across all phases, with the individual pellet diameter increasing from 3⁄32" to 11⁄64" at the onset of phase 3. Various components of the base feed also changed across the three phases, as shown in Tables 2-4. The ground corn content increased at phase 2, for example, at which time dried distillers grain with solubles were also added to the base feed, the concentration of which was then increased at phase 3. The inclusion rates for the respiratory treatment packs remained constant.

TABLE 1

| Days | Dates | Phase | Product Form | Control | Pack 1 | Pack 2 | Pack 3 |
|---|---|---|---|---|---|---|---|
| 10 | Nov. 2, 2020 | 1 | 3⁄32" pellet | A1 | B1 | C1 | D1 |
| 13 | Nov. 12, 2020 | 2 | 3⁄32" pellet | A2 | B2 | C2 | D2 |
| 21 | Nov. 25, 2020 | 3 | 11⁄64" pellet | A3 | B3 | C3 | D3 |

Table 2 shows the details of each feed composition fed to the animals during phase 1 of the trial, with A1 corresponding to the feed composition offered to the control animals, B1 corresponding to the feed composition containing feed pack 1, C1 corresponding to the feed composition containing feed pack 2, and D1 corresponding to the feed composition containing feed pack 3.

TABLE 2

| Ingredient | A1 | B1 | C1 | D1 |
|---|---|---|---|---|
| ground corn fine | 30.02% | 29.94% | 29.93% | 29.94% |
| cereal byproduct | 10% | 10% | 10% | 10% |
| dehulled soymeal | 22.5% | 22.5% | 22.5% | 22.5% |
| processed soy protein | 5.5% | 5.5% | 5.5% | 5.5% |
| poultry meal | 5% | 5% | 5% | 5% |
| lactose source | 18.29% | 18.29% | 18.29% | 18.29% |
| vitamins, minerals, other | 8.69% | 7.7% | 7.7% | 7.7% |
| treatment pack 1 | 0% | 0.07% | 0% | 0% |
| treatment pack 2 | 0% | 0% | 0.1% | 0% |
| treatment pack 3 | 0% | 0% | 0% | 0.07% |

Table 3 shows the details of each feed composition fed during phase 2 of the trial, with A2 corresponding to the feed composition offered to the control animals, B2 corresponding to the feed composition containing feed pack 1, C2 corresponding to the feed composition containing feed pack 2, and D2 corresponding to the feed composition containing feed pack 3.

TABLE 3

| Ingredient | A2 | B2 | C2 | D2 |
|---|---|---|---|---|
| ground corn fine | 53.92% | 53.84% | 53.82% | 53.84% |
| dried distillers grains with solubles | 1.5% | 1.5% | 1.5% | 1.5% |

TABLE 3-continued

| Ingredient | A2 | B2 | C2 | D2 |
|---|---|---|---|---|
| cereal byproduct | 2.5% | 2.5% | 2.5% | 2.5% |
| dehulled soymeal | 26% | 26% | 26% | 26% |
| poultry meal | 5% | 5% | 5% | 5% |
| lactose source | 3.66% | 3.66% | 3.66% | 3.66% |
| vitamins, minerals, other | 7.42% | 7.43% | 7.42% | 7.43% |
| treatment pack 1 | 0% | 0.07% | 0% | 0% |
| treatment pack 2 | 0% | 0% | 0.1% | 0% |
| treatment pack 3 | 0% | 0% | 0% | 0.07% |

Table 4 shows the details of each feed composition fed during phase 3 of the trial, with A3 corresponding to the feed composition offered to the control animals, B3 corresponding to the feed composition containing feed pack 1, C3 corresponding to the feed composition containing feed pack 2, and D3 corresponding to the feed composition containing feed pack 3.

TABLE 4

| Ingredient | A3 | B3 | C3 | D3 |
|---|---|---|---|---|
| ground corn fine | 52% | 51.87% | 51.83% | 51.87% |
| dried distillers grains with solubles | 12% | 12% | 12% | 12% |
| dehulled soymeal | 29.21% | 29.22% | 29.23% | 29.22% |
| vitamins, minerals, other | 6.79% | 6.84% | 6.84% | 6.84% |
| treatment pack 1 | 0% | 0.07% | 0% | 0% |
| treatment pack 2 | 0% | 0% | 0.1% | 0% |
| treatment pack 3 | 0% | 0% | 0% | 0.07% |

The compositions of the feed packs are shown below in Table 5, which details the weight percentage of each active component based on the total weight of each feed pack. As shown, the control feed did not include any of the active components constituting the feed packs, each of which included at least 50 wt % of the C12 DFM composition and a combination of active ingredients including L-ascorbic acid esters, 25-hydroxyvitamin D3, citrus bitter extract flavonoids (*Citrus aurantium*), *Curcuma longa, Capsicum annuum*, a blend of natural essential oils containing thymol and eugenol, and/or *Quillaja saponaria*.

TABLE 5

| Active Component | Control | Pack 1 | Pack 2 | Pack 3 |
|---|---|---|---|---|
| esters of L-ascorbic acid | 0% | 0% | 15.38% | 0% |
| 25-hydroxyvitamin D3 | 0% | 0% | 15.38% | 0% |
| citrus bitter extract flavonoids (citrus aurantium) | 0% | 0% | 10.26% | 0% |
| B. pumilus 1739 and B. pumilus 560 (C12) | 0% | 74.40% | 51.28% | 75.53% |
| curcuma longa + capsicum annuum | 0% | 16.37% | 0% | 0% |
| natural essential oils containing thymol and eugenol | 0% | 0% | 7.69% | 15.11% |
| quillaja saponaria | 0% | 9.23% | 0% | 9.37% |

Feed sampling and analysis involved obtaining one representative, 2-lb. sample of each batch diet, which was then transported to an offsite laboratory for compositional analysis. Individual pigs and feeders were weighed at initiation and on days 10, 23, and 42 post-weaning. Fecal firmness (scored from 1-5: hard-firm-normal-loose-very loose) and color (scored from 1-3: light-medium-dark) were scored by pen two times per week. Fecal scores were used to assess the effects of each feeding regimen on diarrhea status.

The health status and any necessary medication treatments were monitored and recorded on a regular basis. *Streptococcus* symptoms, e.g., shakiness, lethargy, large and red swollen joints, curvy spines, and respiratory stress were monitored and recorded, along with additional respiratory symptoms (e.g., coughing), scours, pig removals, and mortalities. When possible, tissue samples were collected and submitted for lab testing to determine the cause of death.

Individual pig body weights and pen-specific feed intake were used to calculate average daily gain (ADG), average daily feed intake (ADFI), feed-to-gain ratio (feed:gain), and gain-to-feed ratio (gain:feed). Fecal consistency was evaluated on a per-pen basis for the evaluation of treatment effects on diarrhea status. Performance data on ADG, ADFI, feed: gain, and gain:feed were analyzed for overall structure, absence of outliers, and normal distribution using the UNIVARIATE procedure of SAS. Each pen was considered the experimental unit for all data. Experimental data were analyzed as a randomized complete block design using the GLIMMIX procedure of SAS. Significant differences were declared at $P \leq 0.05$ and trends at $P \leq 0.10$.

The growth performance data are presented below in Table 6. As shown, there were no significant differences in ADG, ADFI, or feed:gain ratio among treatments in any phase or overall throughout the study, but the pigs fed the experimental feed products did have greater final body weights compared to the control pigs.

TABLE 6

| | Control | Pack 1 | Pack 2 | Pack 3 | S.E. | P value |
|---|---|---|---|---|---|---|
| initial weight (lbs.) | 13.93 | 13.94 | 13.93 | 13.94 | 0.01 | — |
| weight day 10 (lbs.) | 17.2 | 17.3 | 17.3 | 17.4 | 0.197 | — |
| weight day 23 (lbs.) | 28.5 | 28.3 | 28.6 | 28.3 | 0.391 | — |
| weight day 44 (lbs.) | 55.0 | 55.4 | 55.7 | 55.3 | 0.749 | — |
| ADG days 0-10 (lbs.) | 0.327 | 0.337 | 0.338 | 0.348 | 0.02 | — |
| ADG days 10-23 (lbs.) | 0.863 | 0.843 | 0.868 | 0.832 | 0.026 | — |
| ADG days 23-44 (lbs.) | 1.26 | 1.29 | 1.29 | 1.28 | 0.025 | — |
| ADG days 0-23 (lbs.) | 0.632 | 0.625 | 0.639 | 0.623 | 0.017 | — |
| ADG days 10-44 (lbs.) | 1.11 | 1.12 | 1.13 | 1.11 | 0.022 | — |
| ADG days 0-44 (lbs.) | 0.933 | 0.943 | 0.949 | 0.939 | 0.017 | — |
| ADFI days 0-10 (lbs.) | 0.378 | 0.361 | 0.37 | 0.376 | 0.014 | — |
| ADFI days 10-23 (lbs.) | 1.05 | 1.01 | 1.06 | 1.03 | 0.023 | — |
| ADFI days 23-44 (lbs.) | 1.87 | 1.88 | 1.90 | 1.86 | 0.035 | — |
| ADFI days 0-23 (lbs.) | 0.756 | 0.73 | 0.757 | 0.747 | 0.016 | — |

TABLE 6-continued

| | Control | Pack 1 | Pack 2 | Pack 3 | S.E. | P value |
|---|---|---|---|---|---|---|
| ADFI days 10-44 (lbs.) | 1.55 | 1.55 | 1.58 | 1.54 | 0.026 | — |
| ADFI days 0-44 (lbs.) | 1.29 | 1.28 | 1.30 | 1.28 | 0.02 | — |
| gain:feed days 0-10 | 0.87 | 0.935 | 0.907 | 0.925 | 0.028 | — |
| gain:feed days 10-23 | 0.824 | 0.83 | 0.823 | 0.806 | 0.013 | — |
| gain:feed days 23-44 | 0.677 | 0.688 | 0.682 | 0.694 | 0.013 | — |
| gain:feed days 0-23 | 0.839 | 0.857 | 0.845 | 0.837 | 0.009 | — |
| gain:feed days 10-44 | 0.716 | 0.725 | 0.718 | 0.722 | 0.010 | — |
| gain:feed days 0-44 | 0.727 | 0.739 | 0.732 | 0.737 | 0.010 | — |
| feed:gain days 0-10 | 1.16 | 1.09 | 1.12 | 1.10 | 0.036 | — |
| feed:gain days 10-23 | 1.22 | 1.21 | 1.22 | 1.25 | 0.022 | — |
| feed:gain days 23-44 | 1.48 | 1.45 | 1.48 | 1.45 | 0.029 | — |
| feed:gain days 0-23 | 1.19 | 1.17 | 1.19 | 1.2 | 0.013 | — |
| feed:gain days 10-44 | 1.4 | 1.38 | 1.40 | 1.39 | 0.021 | — |
| feed:gain days 0-44 | 1.38 | 1.35 | 1.37 | 1.36 | 0.019 | — |
| fecal firmness days 0-10 | 3.45 | 3.36 | 3.3 | 3.42 | 0.071 | — |
| fecal firmness days 10-23 | $3.09^{a}$ | $3.18^{ab}$ | $3.25^{b}$ | $3.20^{ab}$ | 0.043 | 0.08 |
| fecal firmness days 23-44 | 3.67 | 3.61 | 3.70 | 3.70 | 0.046 | — |
| fecal firmness days 0-23 | 3.25 | 3.26 | 3.27 | 3.30 | 0.044 | — |
| fecal firmness days 10-44 | 3.44 | 3.44 | 3.52 | 3.5 | 0.033 | — |
| fecal firmness days 0-44 | 3.44 | 3.42 | 3.47 | 3.48 | 0.031 | — |
| fecal color days 0-10 | 1.48 | 1.52 | 1.48 | 1.39 | 0.067 | — |
| fecal color days 10-23 | 2.00 | 2.00 | 1.98 | 2.00 | 0.011 | — |
| fecal color days 23-44 | 2.67 | 2.67 | 2.68 | 2.65 | 0.011 | — |
| fecal color days 0-23 | 1.78 | 1.79 | 1.77 | 1.74 | 0.032 | — |
| fecal color days 10-44 | 2.40 | 2.40 | 2.40 | 2.39 | 0.008 | — |
| fecal color days 0-44 | 2.19 | 2.20 | 2.19 | 2.16 | 0.018 | — |

($^{a,b}$ superscript means different superscripts in the same rows are statistically different ($P < 0.05$))

Health status and pig mortality and removal rates are detailed in Table 7. Compared to the control, feed packs 1, 2, and 3 reduced overall mortality and removal rates (62%, 41%, and 80%, respectively), reduced mortality and removal rates associated with *Streptococcus* symptoms (75%, 26%, and 100%, respectively), and reduced the number of pigs treated for *Streptococcus* symptoms and coughing (53%, 77%, and 53%, respectively).

TABLE 7

| | | | | | % reduction vs. control | | |
|---|---|---|---|---|---|---|---|
| | Control | Pack 1 | Pack 2 | Pack 3 | Pack 1 | Pack 2 | Pack 3 |
| Mortality and Removal Rate (MR) % | 3.9% | 1.5% | 2.3% | 0.78% | −62% | −41% | −80% |
| *Strep.*-linked MR % | 3.1% | 0.78% | 2.3% | 0% | −75% | −26% | −100% |
| % treated for *Strep.* or coughing | 10.1% | 4.7% | 2.3% | 4.7% | −53% | −77% | −53% |
| % treated for *Strep.* | 8.5% | 1.5% | 1.5% | 3.1% | −82% | −82% | −64% |
| % treated for coughing | 1.5% | 3.1% | 0.78% | 1.5% | 107% | −48% | 0% |

Overall, there were not significant differences in growth performance among treatment groups. The experimental feed packs did, however, improve nursery pig health. For example, the feed packs reduced mortality and removal rates (41-80%), especially those associated with symptoms indicative of *Streptococcus* infection (53-77%). The feed packs also reduced the medication treatments necessary to alleviate coughing and *Streptococcus* symptoms (53-77%).

Trial 2

Trial 2 was conducted to determine whether feeding feed products comprising combinations of *Bacillus* with various phytogenic compositions and vitamins can improve the health and performance of nursery pigs. The trial evaluated three experimental feed products or "packs," each containing a unique combination of *Bacillus* strains, vitamins C and D, and phytogenic additives, on the respiratory health and growth performance of nursery pigs over a 42 day span.

Five hundred thirty six weaned pigs averaging 19 days old and weighing 14 lbs. were used in Trial 2, which was also a three-phase feeding trial. At weaning, the pigs were separated by initial body weight and gender and allotted to 44 pens with 11-13 pigs per pen. Pens within each weight block were then assigned to one of four dietary treatments such that there were 11 pens per treatment.

All pigs were housed in a wean-to-finish facility with a concrete floor, five-hole metal feeder, and two nipple waterers. Room temperature was maintained at approximately 78° F. throughout the first week of the trial and then decreased by 3° F. per week thereafter. Room temperatures and humidity levels were recorded daily. Each pen was supplemented with a thermostatically controlled electrical heat mat during the first 14 days post weaning. Pigs were allowed ad libitum access to dry feed and water throughout the study.

One of four different feed compositions was offered to each group of test animals such that each animal group was defined by the unique feed composition offered thereto. The first feed composition was a control consisting of a base feed, only. The second feed composition included the same base feed but supplemented with a feed pack (pack 1), which comprised a DFM composition containing two *Bacillus pumilus* isolates ("C12") and phytogenic blend 1. The third feed composition included the base feed supplemented with feed pack 2, which comprised the C12 DFM composition and phytogenic blend 2. The fourth feed composition included the base feed supplemented with feed pack 3, comprised of a DFM composition containing isolates of *B. amyloliquefaciens* and *B. subtilis* ("C10") and phytogenic blend 3. Each feed composition was offered to the animals in three phases together spanning a total of 42 days. As shown below in Table 8, the first phase spanned days 0-10, the second phase spanned days 10-23, and the third phase spanned days 23-42. The pigs did not receive any antibiotics, whether through feed or water offerings, throughout the study.

TABLE 8

| Days | Dates | Phase | Product Form | Control | Pack 1 | Pack 2 | Pack 3 |
|---|---|---|---|---|---|---|---|
| 10 | Jan. 11, 2021 | 1 | 3/32" pellet | A1 | B1 | C1 | D1 |
| 13 | Jan. 21, 2021 | 2 | 3/32" pellet | A2 | B2 | C2 | D2 |
| 19 | Feb. 3, 2021 | 3 | 11/64" pellet | A3 | B3 | C3 | D3 |

Table 9 shows the details of each feed composition fed during phase 1 of the trial, with A1 corresponding to the feed composition offered to the control animals, B1 corresponding to the feed composition containing feed pack 1, C1 corresponding to the feed composition containing feed pack 2, and D1 corresponding to the feed composition containing feed pack 3.

TABLE 9

| Ingredient | A1 | B1 | C1 | D1 |
|---|---|---|---|---|
| ground corn fine | 29.76% | 29.68% | 29.66% | 29.66% |
| cereal byproduct | 10% | 10% | 10% | 10% |
| dehulled soymeal | 22.5% | 22.5% | 22.5% | 22.5% |
| processed soy protein | 5.5% | 5.5% | 5.5% | 5.5% |
| poultry meal | 5% | 5% | 5% | 5% |
| lactose source | 18.29% | 18.29% | 18.29% | 18.29% |
| vitamins, minerals, other | 8.95% | 8.96% | 8.95% | 8.95% |
| treatment pack 1 | 0% | 0.07% | 0% | 0% |
| treatment pack 2 | 0% | 0% | 0.1% | 0% |
| treatment pack 3 | 0% | 0% | 0% | 0.01% |

Table 10 shows the details of each feed composition fed during phase 2 of the trial, with A2 corresponding to the feed composition offered to the control animals, B2 corresponding to the feed composition containing feed pack 1, C2 corresponding to the feed composition containing feed pack 2, and D2 corresponding to the feed composition containing feed pack 3.

TABLE 10

| Ingredient | A2 | B2 | C2 | D2 |
|---|---|---|---|---|
| ground corn fine | 53.79% | 53.67% | 53.63% | 53.63% |
| dried distillers grains with solubles | 1.5% | 1.5% | 1.5% | 1.5% |
| cereal byproduct | 2.5% | 2.5% | 2.5% | 2.5% |
| dehulled soymeal | 26.13% | 26.14% | 26.14% | 26.14% |
| poultry meal | 5% | 5% | 5% | 5% |
| lactose source | 3.66% | 3.66% | 3.66% | 3.66% |
| vitamins, minerals, other | 7.42% | 7.46% | 7.47% | 7.47% |
| treatment pack 1 | 0% | 0.07% | 0% | 0% |
| treatment pack 2 | 0% | 0% | 0.1% | 0% |
| treatment pack 3 | 0% | 0% | 0% | 0.1% |

Table 11 shows the details of each feed composition fed during phase 3 of the trial, with A3 corresponding to the feed composition offered to the control animals, B3 corresponding to the feed composition containing feed pack 1, C3 corresponding to the feed composition containing feed pack 2, and D3 corresponding to the feed composition containing feed pack 3.

TABLE 11

| Ingredient | A3 | B3 | C3 | D3 |
|---|---|---|---|---|
| ground corn fine | 51.77% | 51.65% | 51.61% | 51.61% |
| dried distillers grains with solubles | 12% | 12% | 12% | 12% |
| dehulled soymeal | 29.25% | 29.26% | 29.26% | 29.26% |
| vitamins, minerals, other | 6.98% | 7.02% | 7.03% | 7.03% |
| treatment pack 1 | 0% | 0.07% | 0% | 0% |
| treatment pack 2 | 0% | 0% | 0.1% | 0% |
| treatment pack 3 | 0% | 0% | 0% | 0.1% |

The details of each feed pack are presented below in Table 12, which shows the weight percentage of each active ingredient based on the total weight of each feed pack. As shown, the control feed did not include any of the active ingredients constituting the feed packs, each of which included at least 50 wt % of either the C12 or C10 DFM composition, along with a combination of active ingredients including L-ascorbic acid esters, 25-hydroxyvitamin D3, citrus bitter extract flavonoids (*Citrus aurantium*), *Curcuma longa, Capsicum annuum*, a blend of natural essential oils containing thymol and eugenol, and/or *Quillaja saponaria*.

TABLE 12

| Active Ingredient | Control | Pack 1 | Pack 2 | Pack 3 |
|---|---|---|---|---|
| *B. pumilus* 1739 and *B. pumilus* 560 (C12) | 0% | 74.40% | 51.28% | 0% |
| curcuma longa + capsicum annuum | 0% | 16.37% | 0% | 0% |
| quillaja saponaria | 0% | 9.23% | 0% | 0% |
| esters of L-ascorbic acid | 0% | 0% | 15.38% | 15.38% |
| 25-hydroxyvitamin D3 | 0% | 0% | 15.38% | 15.38% |

TABLE 12-continued

| Active Ingredient | Control | Pack 1 | Pack 2 | Pack 3 |
|---|---|---|---|---|
| natural essential oil blend containing thymol and eugenol | 0% | 0% | 7.7% | 7.7% |
| citrus bitter extract flavonoids (citrus aurantium) | 0% | 0% | 10.26% | 10.26% |
| *B. amyloliquefaciens* 559 and *Bacillus subtilis* 1024 (C10) | 0% | 0% | 0% | 51.28% |

Feed sampling and analysis involved obtaining one representative, 2-lb. sample of each batch diet, which was then transported to an offsite laboratory for compositional analysis. Individual pigs and feeders were weighed at initiation and on days 10, 23, and 42 post-weaning. Fecal firmness (scored from 1-5: hard-firm-normal-loose-very loose) and color (scored from 1-3: light-medium-dark) were scored by pen two times per week. Fecal scores were used to assess the effects of each feeding regimen on diarrhea status. Blood samples were obtained from each pig on days 9, 17, 24, and 31 post-weaning for complete blood count (CBC) analysis. The same pigs were sampled at each sampling point.

The health status and any necessary medication treatments were monitored and recorded on a regular basis throughout the trial. *Streptococcus* symptoms, e.g., shakiness, lethargy, large and red swollen joints, curvy spines, and respiratory stress, along with additional respiratory symptoms (e.g., coughing), scours, pig removals, and mortalities were all recorded. When possible, tissue samples were collected and submitted for lab testing to determine the cause of death.

Individual pig body weights and pen-specific feed intake were used to calculate average daily gain (ADG), average daily feed intake (ADFI), and feed-to-gain ratio (feed:gain ratio). Fecal consistency was evaluated on a per-pen basis for the evaluation of treatment effects on diarrhea status. Performance data on ADG, ADFI, feed:gain ratio were analyzed for overall structure, absence of outliers, and normal distribution using the UNIVARIATE procedure of SAS. Each pen was considered the experimental unit for all data. Experimental data were analyzed as a randomized complete block design using the GLIMMIX procedure of SAS. Significant differences were declared at $P \leq 0.05$ and trends at $P \leq 0.10$.

The growth performance data are presented below in Table 13. As shown, feed packs 2 and 3 increased ADG (0.27 and 0.27 vs 0.23 lbs.; $P<0.10$) and decreased feed:gain ratios (1.21 and 1.20 vs 1.32; $P<0.10$) compared to the control during phase 1 of the trial. During the second and third phases and overall, none of the feed compositions had any negative impacts on ADG, ADFI, or feed:gain ratio.

TABLE 13

| | | | | | | | P-value relative to control | | |
|---|---|---|---|---|---|---|---|---|---|
| | Control | Pack 1 | Pack 2 | Pack 3 | S.E.M. | P-val. | Pack 1 | Pack 2 | Pack 3 |
| BW, lbs. | | | | | | | | | |
| Initial | 14.05 | 14.02 | 14.04 | 14.05 | 0.854 | 0.63 | 0.26 | 0.71 | 1.00 |
| D 10 | 16.4 | 16.35 | 16.72 | 16.71 | 0.899 | 0.17 | 0.83 | 0.13 | 0.14 |
| D 23 | 26.06 | 25.79 | 26.32 | 25.76 | 1.269 | 0.74 | 0.63 | 0.66 | 0.60 |
| D 30 | 30.97 | 31.15 | 31.73 | 30.95 | 1.415 | 0.61 | 0.78 | 0.26 | 0.97 |
| D 42 | 47.23 | 46.92 | 48.06 | 46.5 | 2.21 | 0.44 | 0.75 | 0.40 | 0.46 |
| Days 0-10 | | | | | | | | | |
| ADG | 0.24 | 0.23 | 0.27 | 0.27 | 0.015 | 0.11 | 0.86 | 0.10 | 0.09 |
| ADFI | 0.3 | 0.29 | 0.32 | 0.32 | 0.015 | 0.19 | 0.68 | 0.19 | 0.19 |
| Feed:Gain | 1.32 | 1.28 | 1.21 | 1.2 | 0.059 | 0.23 | 0.55 | 0.10 | 0.08 |
| Gain:Feed | 0.79 | 0.79 | 0.84 | 0.84 | 0.033 | 0.29 | 0.92 | 0.17 | 0.15 |
| Days 10-23 | | | | | | | | | |
| ADG | 0.74 | 0.72 | 0.73 | 0.69 | 0.037 | 0.6 | 0.68 | 0.79 | 0.21 |
| ADFI | 0.91 | 0.9 | 0.93 | 0.9 | 0.043 | 0.71 | 0.74 | 0.46 | 0.86 |
| Feed:Gain | 1.23 | 1.25 | 1.3 | 1.31 | 0.034 | 0.3 | 0.71 | 0.15 | 0.12 |
| Gain:Feed | 0.81 | 0.8 | 0.78 | 0.77 | 0.019 | 0.3 | 0.70 | 0.19 | 0.10 |
| Days 23-30 | | | | | | | | | |
| ADG | 0.7 | 0.76 | 0.77 | 0.73 | 0.038 | 0.36 | 0.18 | 0.11 | 0.57 |
| ADFI | 1.13[b] | 1.17[ab] | 1.23[a] | 1.13[b] | 0.055 | 0.1 | 0.34 | 0.03 | 0.97 |
| Feed:Gain | 1.62 | 1.55 | 1.61 | 1.55 | 0.046 | 0.61 | 0.33 | 0.99 | 0.36 |
| Gain:Feed | 0.62 | 0.65 | 0.63 | 0.64 | 0.019 | 0.63 | 0.27 | 0.89 | 0.42 |
| Days 30-42 | | | | | | | | | |
| ADG | 1.35 | 1.32 | 1.36 | 1.29 | 0.07 | 0.31 | 0.36 | 0.82 | 0.15 |
| ADFI | 1.87 | 1.88 | 1.89 | 1.83 | 0.094 | 0.64 | 0.96 | 0.71 | 0.39 |
| Feed:Gain | 1.39 | 1.43 | 1.39 | 1.42 | 0.016 | 0.18 | 0.05 | 0.81 | 0.23 |
| Gain:Feed | 0.72 | 0.7 | 0.72 | 0.71 | 0.007 | 0.13 | 0.04 | 0.93 | 0.20 |
| Days 0-23 | | | | | | | | | |
| ADG | 0.52 | 0.51 | 0.53 | 0.51 | 0.023 | 0.73 | 0.61 | 0.69 | 0.56 |
| ADFI | 0.64 | 0.63 | 0.66 | 0.65 | 0.03 | 0.62 | 0.66 | 0.40 | 0.78 |
| Feed:Gain | 1.23 | 1.25 | 1.26 | 1.27 | 0.029 | 0.69 | 0.62 | 0.40 | 0.25 |
| Gain:Feed | 0.82 | 0.81 | 0.8 | 0.79 | 0.018 | 0.71 | 0.71 | 0.54 | 0.26 |
| Days 10-30 | | | | | | | | | |
| ADG | 0.72 | 0.74 | 0.74 | 0.71 | 0.032 | 0.57 | 0.68 | 0.48 | 0.53 |
| ADFI | 0.99 | 1 | 1.04 | 0.98 | 0.045 | 0.3 | 0.77 | 0.12 | 0.86 |

TABLE 13-continued

| | Control | Pack 1 | Pack 2 | Pack 3 | S.E.M. | P-val. | P-value relative to control Pack 1 | Pack 2 | Pack 3 |
|---|---|---|---|---|---|---|---|---|---|
| Feed:Gain | 1.36 | 1.35 | 1.4 | 1.39 | 0.021 | 0.28 | 0.75 | 0.18 | 0.30 |
| Gain:Feed | 0.73 | 0.74 | 0.72 | 0.72 | 0.012 | 0.29 | 0.70 | 0.19 | 0.10 |
| Days 0-30 | | | | | | | | | |
| ADG | 0.57 | 0.57 | 0.59 | 0.56 | 0.023 | 0.64 | 0.87 | 0.31 | 0.87 |
| ADFI | 0.76 | 0.76 | 0.8 | 0.76 | 0.034 | 0.31 | 0.97 | 0.12 | 0.91 |
| Feed:Gain | 1.34 | 1.34 | 1.36 | 1.35 | 0.021 | 0.84 | 0.69 | 0.69 | 0.84 |
| Gain:Feed | 0.75 | 0.75 | 0.74 | 0.74 | 0.012 | 0.87 | 0.82 | 0.55 | 0.71 |
| Days 10-42 | | | | | | | | | |
| ADG | 0.96 | 0.95 | 0.97 | 0.93 | 0.044 | 0.37 | 0.80 | 0.61 | 0.23 |
| ADFI | 1.32 | 1.33 | 1.36 | 1.3 | 0.062 | 0.4 | 0.81 | 0.25 | 0.59 |
| Feed:Gain | 1.37 | 1.39 | 1.39 | 1.4 | 0.013 | 0.47 | 0.29 | 0.29 | 0.13 |
| Gain:Feed | 0.73 | 0.72 | 0.72 | 0.71 | 0.007 | 0.61 | 0.46 | 0.35 | 0.20 |
| Days 23-42 | | | | | | | | | |
| ADG | 1.11 | 1.11 | 1.14 | 1.09 | 0.053 | 0.35 | 0.89 | 0.36 | 0.37 |
| ADFI | 1.6 | 1.62 | 1.65 | 1.57 | 0.076 | 0.32 | 0.67 | 0.25 | 0.50 |
| Feed:Gain | 1.44 | 1.46 | 1.44 | 1.45 | 0.016 | 0.81 | 0.38 | 0.79 | 0.54 |
| Gain:Feed | 0.7 | 0.69 | 0.69 | 0.69 | 0.008 | 0.82 | 0.36 | 0.83 | 0.62 |
| Days 0-42 | | | | | | | | | |
| ADG | 0.79 | 0.78 | 0.81 | 0.77 | 0.034 | 0.48 | 0.76 | 0.42 | 0.49 |
| ADFI | 1.08 | 1.08 | 1.11 | 1.07 | 0.05 | 0.43 | 0.92 | 0.23 | 0.70 |
| Feed:Gain | 1.36 | 1.38 | 1.37 | 1.38 | 0.013 | 0.71 | 0.31 | 0.54 | 0.36 |
| Gain:Feed | 0.73 | 0.73 | 0.73 | 0.73 | 0.007 | 0.73 | 0.29 | 0.56 | 0.34 |

($^{a,b}$ superscript means different superscripts in the same rows are statistically different ($P < 0.05$))

Health observations and pig mortality and removal rates are detailed in Table 14. As shown, feed packs 1 and 3 numerically reduced mortality and removal rates compared to the control (2.24% and 3.73% vs 4.48%, respectively for treatment packs 1, 3 and control). In addition, all feed packs numerically reduced the percentage of pigs that received medication through injection (20.90%, 17.91%, and 16.42% vs 23.88% respectively for feed packs 1, 2, 3, and control) and percentage of pigs treated for *Streptococcus* symptoms (8.21%, 8.21%, and 8.21% vs 11.94% respectively for treatment packs 1, 2, 3, and control). Feed packs 2 and 3 numerically reduced the percentage of pigs treated for swollen joint and lame symptoms (4.48% and 5.22% vs 8.21% respectively for treatment packs 2, 3 and the control). No major differences among treatments on fecal firmness were observed.

TABLE 14

| | Treatments Control | Pack 1 | Pack 2 | Pack 3 |
|---|---|---|---|---|
| MR % | 4.48 | 2.24 | 5.97 | 3.73 |
| Strep.-linked MR % | 3.73 | 2.24 | 5.97 | 3.73 |
| total % treated | 23.88 | 20.90 | 17.91 | 16.42 |
| % treated for Strep. | 11.94 | 8.21 | 8.21 | 8.21 |
| % treated for swollen joints and lame | 8.21 | 8.96 | 4.48 | 5.22 |
| % treated for other symptoms | 3.73 | 3.73 | 5.22 | 2.99 |

The effects of each feed pack on complete blood count varied. Feed pack 1 reduced white blood cell ($P<0.05$) and granulocyte ($P<0.01$) counts on day 9 post-weaning; however, this reduction disappeared at later timepoints. Feed packs 1 and 3 increased the lymphocyte percentage on day 9 compared to the control. Feed pack 1 numerically reduced the white blood cell:lymphocyte ratio compared to the control (1.63 vs. 1.78). The white blood cells and white blood cells-to-lymphocyte ratio (WBC:LYM) are considered markers of systemic inflammation. In this trial, *Streptococcus*-associated health symptoms were observed throughout the study. The decrease of WBC:LYM ratio in pigs fed feed pack 1 suggests that this feed product may reduce the inflammation of pigs afflicted with health issues, including respiratory stress. This observation is consistent with the lower mortality and removal rate observed in pigs fed feed pack 1, as shown above in Table 14.

In sum, the experimental feed packs did not have any negative impact on feed intake or animal performance. During the first 10 days post-weaning, feed packs 2 and 3 actually increased the ADG and feed conversion compared to the control. This effect was not observed in pigs fed feed pack 1. Feeding feed pack 1 numerically reduced total mortality and removal rates and mortality and removal rate associated to *Streptococcus* symptoms. All feed packs tested in Trial 2 numerically reduced the percentage of pigs that received medication through injection and the percentage of pigs treated for *Streptococcus* symptoms compared to the control pigs.

Trial 3

Trial 3 was conducted to determine whether feeding feed products comprising combinations of *Bacillus* with various phytogenic compositions and vitamins can improve the health and performance of growing pigs. The trial evaluated three experimental feed products or "packs," each containing a unique combination of *Bacillus* strains, vitamins C and D, and phytogenic additives on the respiratory health and growth performance of growing pigs over a 59 day span.

Four hundred thirty five pigs averaging 19 days old and weighing 48 lbs. were used in Trial 3, which was also a three-phase feeding trial. At weaning, the pigs were separated by initial body weight and gender and allotted to 44 pens with 9-10 pigs per pen. Pens within each weight block were then assigned to one of four dietary treatments, which continued post-grower (except treatment 2), such that there were 11 pens per treatment.

All pigs were housed in a wean-to-finish facility with a concrete floor, five-hole metal feeder, and two nipple waterers. Room temperature was maintained at approximately 76° F. throughout the first week of the trial and then decreased by 3° F. per week thereafter. Room temperatures and humidity levels were recorded daily. Pigs were allowed ad libitum access to dry feed and water throughout the study.

One of four different feed compositions was offered to each group of test animals such that each animal group was defined by the unique feed composition offered thereto. The first feed composition was a control consisting of a base feed, only. The second feed composition included the same base feed but supplemented with a feed pack (pack 1), which comprised a DFM composition containing two *Bacillus pumilus* isolates ("C12") and phytogenic blend 1. The third feed composition included the base feed supplemented with feed pack 2, which comprised the C12 DFM composition and phytogenic blend 2. The fourth feed composition included the base feed supplemented with feed pack 3, comprised of a DFM composition containing isolates of *B. amyloliquefaciens* and *B. subtilis* ("C10") and phytogenic blend 2. Each feed composition was offered to the animals in three phases together spanning a total of 59 days. As shown below in Table 15, the first phase spanned days 0-16, the second phase spanned days 16-38, and the third phase spanned days 38-59. All feed compositions comprised a base mixture of corn, soybean meal, and dried distillers grains with solubles. All feed compositions were also non-medicated and formulated to be isonitrogenous and isoenergetic. Standardized ileal digestibility ("SID") amino acid levels, fat, vitamins, and minerals were maintained at similar levels between the feed compositions. The compositions were formulated to contain 1.15%, 1.05%, and 0.95% SID lysine for phases 1, 2, and 3, respectively. The test and control pigs did not receive any antibiotics, whether through feed or water offerings, throughout the study.

TABLE 15

| Days | Dates | Phase | Product Form | Est. BW (lbs.) | Control | Pack 1 | Pack 2 | Pack 3 |
|---|---|---|---|---|---|---|---|---|
| 16 | Feb. 22, 2021 | 1 | Meal | ~50-80 | A1 | B1 | C1 | D1 |
| 38 | Mar. 10, 2021 | 2 | Meal | ~80-120 | A2 | B2 | C2 | D2 |
| 59 | Apr. 1, 2021 | 3 | Meal | ~120-170 | A3 | B3 | C3 | D3 |

Table 16 shows the details of each feed composition fed to the animals during phase 1 of the trial, with A1 corresponding to the feed composition offered to the control animals, B1 corresponding to the feed composition containing feed pack 1, C1 corresponding to the feed composition containing feed pack 2, and D1 corresponding to the feed composition containing feed pack 3.

TABLE 16

| Ingredient | A1 | B1 | C1 | D1 |
|---|---|---|---|---|
| ground corn coarse | 56% | 55.86% | 55.83% | 55.83% |
| dried distillers grains with solubles | 15% | 15% | 15% | 15% |
| dehulled soymeal | 24.51% | 24.52% | 24.52% | 24.52% |
| choice white grease | 2.36% | 2.39% | 2.42% | 2.42% |
| vitamins, minerals, other | 2.13% | 2.13% | 2.13% | 2.13% |
| treatment pack 1 | 0% | 0.1% | 0% | 0% |
| treatment pack 2 | 0% | 0% | 0.1% | 0% |
| treatment pack 3 | 0% | 0% | 0% | 0.1% |

Table 17 shows the details of each feed composition fed during phase 2 of the trial, with A2 corresponding to the feed composition offered to the control animals, B2 corresponding to the feed composition containing feed pack 1, C2 corresponding to the feed composition containing feed pack 2, and D2 corresponding to the feed composition containing feed pack 3.

TABLE 17

| Ingredient | A2 | B2 | C2 | D2 |
|---|---|---|---|---|
| ground corn coarse | 56.11% | 56% | 55.95% | 55.95% |
| dried distillers grains with solubles | 20% | 20% | 20% | 20% |
| dehulled soymeal | 19.61% | 19.62% | 19.62% | 19.62% |
| choice white grease | 2.26% | 2.28% | 2.31% | 2.31% |
| vitamins, minerals, other | 2.02% | 2.02% | 2.02 | 2.02 |
| treatment pack 1 | 0% | 0.1% | 0% | 0% |
| treatment pack 2 | 0% | 0% | 0.1% | 0% |
| treatment pack 3 | 0% | 0% | 0% | 0.1% |

Table 18 shows the details of each feed composition fed during phase 3 of the trial, with A3 corresponding to the feed composition offered to the control animals, B3 corresponding to the feed composition containing feed pack 1, C3 corresponding to the feed composition containing feed pack 2, and D3 corresponding to the feed composition containing feed pack 3. As shown, the inclusion rates for the feed packs were reduced compared to phases 1 and 2.

TABLE 18

| Ingredient | A3 | B3 | C3 | D3 |
|---|---|---|---|---|
| ground corn coarse | 60.14% | 60.07% | 60.06% | 60.06% |
| dried distillers grains with solubles | 20% | 20% | 20% | 20% |
| dehulled soymeal | 15.88% | 15.88% | 15.88% | 15.88% |
| choice white grease | 1.98% | 1.99% | 2% | 2% |
| vitamins, minerals, other | 2% | 2.01% | 2.01% | 2.01% |
| treatment pack 1 | 0% | 0.05% | 0% | 0% |
| treatment pack 2 | 0% | 0% | 0.05% | 0% |
| treatment pack 3 | 0% | 0% | 0% | 0.05% |

The composition of each feed pack is shown below in Table 19, which details the weight percentage of each active component based on the total weight of each feed pack. As shown, the control feed did not include any of the active components of the feed packs, each of which included at least 50 wt % of the C12 or C10 DFM composition and a combination of active ingredients including L-ascorbic acid esters, 25-hydroxyvitamin D3, citrus bitter extract flavonoids (*Citrus aurantium*), and a blend of natural essential oils containing thymol and eugenol.

TABLE 19

| Active | Phases 1-3 | | | |
|---|---|---|---|---|
| Component | Con. | Pack 1 | Pack 2 | Pack 3 |
| *B. pumilus* 1739 and *B. pumilus* 560 (C12) | 0 | 52.63 | 51.28 | 0 |
| medium chain fatty acid | 0 | 39.5 | 0 | 0 |
| garlic supplement | 0 | 7.89 | 0 | 0 |
| esters of L-ascorbic acid | 0 | 0 | 15.38 | 15.38 |
| 25-hydroxyvitamin D3 | 0 | 0 | 15.38 | 15.38 |
| citrus bitter extract flavonoids (citrus aurantium) | 0 | 0 | 10.26 | 10.26 |
| natural essential oils containing thymol and eugenol | 0 | 0 | 7.7 | 7.7 |
| *B. amyloliquefaciens* 559 and *Bacillus subtilis* 1024 (C10) | 0 | 0 | 0 | 51.28 |

Feed sampling and analysis involved obtaining one representative, 2-lb. sample of each batch diet, which was then transported to an offsite laboratory for compositional analysis. Individual pigs and feeders were weighed at initiation and on days 16, 38, and 59 post-grower. Fecal firmness (scored from 1-5: hard-firm-normal-loose-very loose) and color (scored from 1-3: light-medium-dark) were scored by pen two times per week. Fecal scores were used to assess the effects of each feeding regimen on diarrhea status.

The health status and any necessary medication treatments were monitored and recorded on a regular basis throughout the trial. *Streptococcus* symptoms, e.g., shakiness, lethargy, large and red swollen joints, curvy spines, and respiratory stress, along with additional respiratory symptoms (e.g., coughing), scours, pig removals, and mortalities were all recorded. When possible, tissue samples were collected and submitted for lab testing to determine the cause of death.

Individual pig body weights and pen-specific feed intake were used to calculate average daily gain (ADG), average daily feed intake (ADFI), and feed-to-gain ratio (feed:gain). Fecal consistency was evaluated on a per-pen basis for the evaluation of treatment effects on diarrhea status. Performance data on ADG, ADFI, and feed:gain were analyzed for overall structure, absence of outliers, and normal distribution using the UNIVARIATE procedure of SAS. Each pen was considered the experimental unit for all data. Experimental data were analyzed as a randomized complete block design using the GLIMMIX procedure of SAS. Significant differences were declared at $P \leq 0.05$ and trends at $P \leq 0.10$.

The growth performance data are presented below in Table 20. As shown, pigs fed packs 1, 2, and 3 exhibited increases in body weight gain of 2.3%, 2.8%, and 2.8%, respectively, over the 59-day duration of the trial relative to the control animals, resulting in final body weights respectively 2.9 pounds, 4.1 pounds, and 3.3 pounds heavier than the control animals. Pigs fed a feed pack containing esters of ascorbic acid, 25-hydroxyvitamin D3, and natural essential oils with C12 (pack 2) or C10 (pack 3) performed the best, increasing gain by 2.8%, consuming less feed by 2.0%, and improving feed conversion by 1%. Providing feed packs 1 and 3 also reduced body weight variation relative to the control animals.

TABLE 20

| | | | | | | P Values | | | |
|---|---|---|---|---|---|---|---|---|---|
| | Con. | Pack 1 | Pack 2 | Pack 3 | SEM | Treatment effect | Con. vs. Pack 1 | Con. vs. Pack 2 | Con. vs. Pack 3 |
| Body Weight, lbs. | | | | | | | | | |
| Initial | 48.4 | 48.3 | 48.6 | 47.7 | 2.0 | 0.67 | 0.82 | 0.84 | 0.34 |
| 16 d | 74.0 | 74.7 | 74.7 | 73.9 | 2.8 | 0.79 | 0.50 | 0.55 | 0.89 |
| 38 d | 121.9 | 124.0 | 123.8 | 124.5 | 3.7 | 0.35 | 0.16 | 0.22 | 0.10 |
| 59 d | 177.0 | 179.9 | 181.1 | 180.3 | 4.4 | 0.17 | 0.14 | 0.04 | 0.09 |
| Body Weight Standard Deviation, lbs. | | | | | | | | | |
| Initial | 6.05 | 5.77 | 5.30 | 5.70 | 0.46 | 0.68 | 0.65 | 0.23 | 0.57 |
| 16 d | 9.36 | 8.69 | 7.90 | 8.43 | 0.62 | 0.43 | 0.45 | 0.11 | 0.30 |
| 38 d | 13.50 | 11.38 | 11.24 | 11.28 | 0.75 | 0.11 | 0.05 | 0.04 | 0.04 |
| 59 d | 16.34[e] | 13.93[f] | 14.42[ef] | 13.4[f] | 0.83 | 0.09 | 0.05 | 0.11 | 0.02 |
| D 0-16 | | | | | | | | | |
| ADG, lb | 1.60 | 1.66 | 1.63 | 1.64 | 0.05 | 0.33 | 0.07 | 0.34 | 0.25 |
| ADFI, lb | 2.65 | 2.70 | 2.66 | 2.67 | 0.10 | 0.73 | 0.30 | 0.82 | 0.79 |
| Feed:Gain | 1.65 | 1.63 | 1.63 | 1.63 | 0.01 | 0.25 | 0.13 | 0.13 | 0.07 |
| D 16-38 | | | | | | | | | |
| ADG, lb | 2.17[d] | 2.24[c] | 2.22[cd] | 2.27[c] | 0.05 | 0.03 | 0.05 | 0.11 | 0.004 |
| ADFI, lb | 4.37 | 4.52 | 4.44 | 4.50 | 0.12 | 0.23 | 0.06 | 0.35 | 0.09 |
| Feed:Gain | 2.01 | 2.02 | 1.99 | 1.98 | 0.02 | 0.36 | 0.97 | 0.37 | 0.15 |
| D 38-59 | | | | | | | | | |
| ADG, lb | 2.62 | 2.66 | 2.72 | 2.66 | 0.05 | 0.13 | 0.38 | 0.02 | 0.37 |
| ADFI, lb | 6.08 | 6.19 | 6.24 | 6.17 | 0.18 | 0.47 | 0.28 | 0.13 | 0.35 |
| Feed:Gain | 2.31 | 2.33 | 2.29 | 2.32 | 0.03 | 0.65 | 0.72 | 0.41 | 0.91 |

TABLE 20-continued

| | Con. | Pack 1 | Pack 2 | Pack 3 | SEM | P Values Treatment effect | Con. vs. Pack 1 | Con. vs. Pack 2 | Con. vs. Pack 3 |
|---|---|---|---|---|---|---|---|---|---|
| D 0-38 | | | | | | | | | |
| ADG, lb | 1.93[d] | 1.99[c] | 1.98[c] | 2.01[c] | 0.05 | 0.04 | 0.03 | 0.10 | 0.01 |
| ADFI, lb | 3.65 | 3.75 | 3.69 | 3.73 | 0.11 | 0.32 | 0.08 | 0.43 | 0.17 |
| Feed:Gain | 1.89 | 1.88 | 1.87 | 1.85 | 0.02 | 0.37 | 0.75 | 0.32 | 0.11 |
| D 16-59 | | | | | | | | | |
| ADG, lb | 2.39[f] | 2.44[e] | 2.47[e] | 2.46[e] | 0.05 | 0.07 | 0.10 | 0.02 | 0.03 |
| ADFI, lb | 5.20 | 5.33 | 5.32 | 5.32 | 0.14 | 0.38 | 0.13 | 0.18 | 0.17 |
| Feed:Gain | 2.17 | 2.18 | 2.15 | 2.16 | 0.02 | 0.52 | 0.79 | 0.30 | 0.46 |
| D 0-59 | | | | | | | | | |
| ADG, lb | 2.18[b] | 2.23[a] | 2.24[a] | 2.24[a] | 0.05 | 0.05 | 0.05 | 0.02 | 0.01 |
| ADFI, lb | 4.51 | 4.62 | 4.60 | 4.60 | 0.12 | 0.38 | 0.11 | 0.20 | 0.20 |
| Feed:Gain | 2.07 | 2.07 | 2.05 | 2.05 | 0.02 | 0.60 | 0.93 | 0.32 | 0.41 |

Table 21 shows the effects of each respiratory pack on the health status of growing pigs throughout the trial. Feeding the feed packs numerically decreased the number of pigs treated by medication. Among the packs, pack 3 corresponded to the lowest number of treated pigs relative to the control pigs. No significant differences on fecal firmness were observed between the treatments.

TABLE 21

| Observations | Control | Pack 1 | Pack 2 | Pack 3 |
|---|---|---|---|---|
| Number of pigs died/removed | 2 | 1 | 3 | 2 |
| Number of pigs treated for Streptococcus symptoms, coughing, PCV3 | 3 | 1 | 1 | 1 |
| Number of pigs treated for swollen joints, lame, prolapse, belly rupture, skinny, tail chewed | 1 | 2 | 2 | 0 |

Overall, all test packs improved weight gain and feed intake, and packs 2 and 3 additionally improved feed conversion. Pack 3 performed the best with respect to improving total gain, feed intake, and feed efficiency, while also reducing the number of pigs that required medication.

Trial 4

Trial 4 was conducted to determine whether feeding feed products comprising combinations of *Bacillus* with various phytogenic compositions and vitamins can improve pig health and performance during the growing phase. The experiment evaluated three experimental feed packs, each containing a unique combination of *Bacillus*, vitamins C and D, and phytogenic additives, on the respiratory health and growth performance of growing pigs over a 56 day span.

At the end of the nursery period, all test pigs were weighed. The average age was 9 weeks and the average initial body weight was 55 lbs. The pigs were sorted by weight and gender and blocked into 15 weight blocks (or "replications") of 20 or 24 pigs per group. Pigs within each weight block were allotted into four equal groups of pens (replications 1-8 had 6 pigs/pen; replications 9-15 had 5 pigs/pen). Dietary treatments were randomly assigned to pens within each of the weight groups (15 pens/treatment).

Pigs were housed in four environmentally controlled finishing rooms. In rooms 1 and 2, pigs were housed in 5'×9' pens with 5 pigs per pen. In rooms 3 and 4, pigs were housed in 5'×10' pens with 6 pigs per pen. All pens had concrete slatted floors and a nipple waterer. Room temperature, humidity readings, and water meter readings were taken daily throughout the study. Pigs were provided ad libitum access to dry feed and water and were monitored according to the routine health procedures.

One of four different feed compositions was offered to each group of testing animals, such that each group was defined by the unique feed composition offered thereto. The first feed composition was a control consisting of a base feed, only, which comprised a mixture of corn, soybean meal, dried distiller grains, but no DFMs, phytogenics or vitamin additives. The second feed composition included in the same base feed but supplemented with a feed pack (pack 1), which comprised *Quillaja saponaria, Curcuma longa, Capsicum annuum*, and a mixture of *B. amyloliquefaciens* 559 and *Bacillus subtilis* 1024 isolates ("C10"). The third feed composition included a base feed supplemented with a second feed pack (pack 2), which comprised esters of L-ascorbic acid, 25-hydroxyvitamin D3, citrus bitter extract flavonoids (*Citrus aurantium*), thymol, eugenol, and C10. The fourth feed composition included the base feed supplemented with a third feed pack (pack 3), which comprised *Quillaja saponaria*, thymol, eugenol, and C10. Each feed composition was offered to the animals in four phases. As shown, below in Table 22, the first phase spanned 17 days, during which the pigs ranged from 55-85 pounds. The second phase spanned 13 days, during which the pigs ranged from 85-115 pounds. The third phase spanned 13 days, during which the pigs were 115-145 pounds, and the fourth phase also spanned 13 days, during which the pigs ranged from 145-180 pounds. Throughout the four phases, the ratio of active components within the experimental feed packs remained constant, while the weight percentage of the feed packs within the broader feed compositions varied slightly, changing for example between phases 2 and 3.

TABLE 22

| Days | Est. BW (lbs.) | Phase | Control | Pack 1 | Pack 2 | Pack 3 |
|---|---|---|---|---|---|---|
| 17 | ~55-85 | 1 | A1 | B1 | C1 | D1 |
| 13 | ~85-115 | 2 | A2 | B2 | C2 | D2 |
| 13 | ~115-145 | 3 | A3 | B3 | C3 | D3 |
| 13 | ~145-180 | 4 | A4 | B4 | C4 | D4 |

Table 23 shows the details of each feed composition fed to the animals during phase 1 of the trial, with A1 corresponding to the feed composition offered to the control animals, B1 corresponding to the feed composition containing feed pack 1, C1 corresponding to the feed composition containing feed pack 2, and D1 corresponding to the feed composition containing feed pack 3.

TABLE 23

| Ingredient | A1 | B1 | C1 | D1 |
|---|---|---|---|---|
| ground corn coarse | 55.67% | 55.56% | 55.52% | 55.56% |
| dried distillers grains with solubles | 15% | 15% | 15% | 15% |
| dehulled soymeal | 24.67% | 24.68% | 24.68% | 24.68% |
| choice white grease | 2.52% | 2.56% | 2.57% | 2.55% |
| vitamins, minerals, other | 2.14% | 2.13% | 2.13% | 2.14% |
| treatment pack 1 | 0% | 0.07% | 0% | 0% |
| treatment pack 2 | 0% | 0% | 0.1% | 0% |
| treatment pack 3 | 0% | 0% | 0% | 0.07% |

Table 24 shows the details of each feed composition fed during phase 2 of the trial, with A2 corresponding to the feed composition offered to the control animals, B2 corresponding to the feed composition containing feed pack 1, C2 corresponding to the feed composition containing feed pack 2, and D2 corresponding to the feed composition containing feed pack 3.

TABLE 24

| Ingredient | A2 | B2 | C2 | D2 |
|---|---|---|---|---|
| ground corn coarse | 56.02% | 55.90% | 55.86% | 55.91% |
| dried distillers grains with solubles | 20% | 20% | 20% | 20% |
| dehulled soymeal | 19.86% | 19.86% | 19.87% | 19.86% |
| choice white grease | 2.10% | 2.14% | 2.15% | 2.14% |
| vitamins, minerals, other | 2.02% | 2.03% | 2.02% | 2.02% |
| treatment pack 1 | 0% | 0.07% | 0% | 0% |
| treatment pack 2 | 0% | 0% | 0.1% | 0% |
| treatment pack 3 | 0% | 0% | 0% | 0.07% |

Table 25 shows the details of each feed composition fed during phase 3 of the trial, with A3 corresponding to the feed composition offered to the control animals, B3 corresponding to the feed composition containing feed pack 1, C3 corresponding to the feed composition containing feed pack 2, and D3 corresponding to the feed composition containing feed pack 3. As shown, the weight percentage of coarse ground corn increased relative to phases 1 and 2, and the weight percentage of the feed packs decreased relative to phases 1 and 2.

TABLE 25

| Ingredient | A3 | B3 | C3 | D3 |
|---|---|---|---|---|
| ground corn coarse | 60.34% | 60.29% | 60.27% | 60.29% |
| dried distillers grains with solubles | 20% | 20% | 20% | 20% |
| dehulled soymeal | 15.68% | 15.69% | 15.69% | 15.69% |
| choice white grease | 1.97% | 1.99% | 2.00% | 1.99% |
| vitamins, minerals, other | 2.01% | 2.00% | 1.99% | 2.00% |
| treatment pack 1 | 0% | 0.03% | 0% | 0% |
| treatment pack 2 | 0% | 0% | 0.05% | 0% |
| treatment pack 3 | 0% | 0% | 0% | 0.03% |

Table 26 shows the details of each feed composition fed during phase 4 of the trial, with A4 corresponding to the feed composition offered to the control animals, B4 corresponding to the feed composition containing feed pack 1, C4 corresponding to the feed composition containing feed pack 2, and D4 corresponding to the feed composition containing feed pack 3. As shown, the weight percentage of coarse ground corn increased relative to phases 1, 2, and 3, while the weight percentage of dried distillers grains with solubles decreased relative to the preceding phases. The inclusion rate of each feed pack remained consistent with phase 3.

TABLE 26

| Ingredient | A4 | B4 | C4 | D4 |
|---|---|---|---|---|
| ground corn coarse | 73.15% | 73.09% | 73.07% | 73.09% |
| dried distillers grains with solubles | 10% | 10% | 10% | 10% |
| dehulled soymeal | 12.98% | 12.98% | 12.98% | 12.98% |
| choice white grease | 1.54% | 1.56% | 1.57% | 1.56% |
| vitamins, minerals, other | 2.33% | 2.34% | 2.33% | 2.34% |
| treatment pack 1 | 0% | 0.03% | 0% | 0% |
| treatment pack 2 | 0% | 0% | 0.05% | 0% |
| treatment pack 3 | 0% | 0% | 0% | 0.03% |

The composition of each feed pack is shown below in Table 27, which details the weight percentage of each active component based on the total weight of each feed pack. As shown, the control feed did not include any of the active components of the feed packs, each of which included at least 50 wt % of the C10 DFM composition and a combination of active ingredients including L-ascorbic acid esters, 25-hydroxyvitamin D3, citrus bitter extract flavonoids (*Citrus aurantium*), and a blend of natural essential oils containing thymol and eugenol.

TABLE 27

| | Phases 1-4 | | | |
|---|---|---|---|---|
| Active Component | Control | Pack 1 | Pack 2 | Pack 3 |
| Quillaja Saponaria | 0 | 9.23 | 0 | 9.37 |
| Curcuma longa and Capsicum annuum | 0 | 16.37 | 0 | 0 |
| esters of L-ascorbic acid | 0 | 0 | 15.38 | 0 |
| 25-hydroxyvitamin D3 | 0 | 0 | 15.38 | 0 |
| citrus bitter extract flavonoids (citrus aurantium) | 0 | 0 | 10.26 | 0 |
| natural essential oils containing thymol and eugenol | 0 | 0 | 7.7 | 15.11 |
| B. amyloliquefaciens 559 and Bacillus subtilis 1024 (C10) | 0 | 74.40 | 51.28 | 75.53 |

Individual pigs and feeders were weighted at initiation, day 17, day 30, day 43, and day 56 for the calculation of average daily gain, average daily feed intake, and feed:gain ratio. Fecal firmness (scored from 1 to 5: hard-firm-normal-loose-very loose) and color (scored from 1 to 3: light-medium-dark) were scored on a pen-basis two times a week. Fecal scores were used to access the effects of dietary treatments on diarrhea status. On days 14 and 42, blood samples were collected from one pig/pen and used for complete blood count (CBC) analysis. The same pigs were sampled at both sampling points.

Individual body weights and pen feed intake were used to calculate ADG, ADFI, and feed:gain ratio. Fecal consistency was evaluated per pen for the evaluation of treatment effects on diarrhea status. All data, i.e., body weight, ADG, ADFI, feed:gain, and carcass characteristics, were analyzed for overall structure, absence of outliers, and normal distribution using the UNIVARIATE procedure of SAS (SAS 9.4; SAS Institute, Cary, NC). A randomized complete block design was used to test the effect of dietary treatments. All data were analyzed by Analysis of Variance with mixed models using GLIMMIX procedure of SAS and least squares means were compared using Fisher's least significant difference. A pen was considered the experimental unit for all data, and the significant differences were declared at P≤0.05 and trends at P≤0.10. Pigs were observed closely for signs of illness, including *Streptococcus* symptoms, coughing, other illness, as well as the need for medication-based treatments.

The animal performance data are presented in Table 28. During days 0-30, all test pigs exhibited improved weight gain and feed:gain ratio relative to the pigs in the control group. From days 30-56, pigs fed pack 3 had a 3.1% greater ADG and a 3.1% greater ADFI while having a similar feed:gain ratio compared to the control animals. Over days 0-56, all test pigs had a greater ADG (by 1.3%, 1.7%, and 3.0%, respectively for pack 1, 2, and 3) and feed:gain (by 2.3%, 1.9%, and 0.9%, respectively for pack 1, 2, and 3) compared to the control. Among the three experimental feed packs evaluated in this study, pack 3 was the most efficient in improving gain (by 3.0%; P=0.18) resulting in 4.3 lbs. heavier pigs compared to the control. Pigs fed pack 1 and pack 2 were the most efficient in improving feed:gain relative to the control animals. The feed packs notably did not have a negative impact on the test pigs' blood CBC profile or fecal firmness.

TABLE 28

| | | | | | | P Values, | Improvement over Control | | |
|---|---|---|---|---|---|---|---|---|---|
| | Con. | Pack 1 | Pack 2 | Pack 3 | SEM | Treatment effect | Pack 1 vs. Con. | Pack 2 vs. Con | Pack 3 vs. Con |
| Body Weight, lbs. | | | | | | | | | |
| Initial | 62.4 | 62.4 | 62.5 | 62.5 | 1.38 | 0.98 | 0 | 0.1 | 0.1 |
| 17 d | 94.6 | 95.5 | 95.7 | 95.6 | 1.32 | 0.21 | 0.9 | 1.1 | 1.0 |
| 30 d | 125.6 | 126.7 | 127.4 | 127.6 | 1.80 | 0.27 | 1.1 | 1.8 | 2.0 |
| 43 d | 158.9c | 159.9bc | 161.4ab | 162.4a | 2.08 | 0.08 | 1.0 | 2.5 | 3.5 |
| 56 d | 192.5b | 194.3ab | 195.1ab | 196.8a | 2.53 | 0.09 | 1.8 | 2.6 | 4.3 |
| D 0-17 | | | | | | | | | |
| ADG, lb | 1.95 | 2.01 | 2.02 | 2.01 | 0.03 | 0.21 | 3.1% | 3.6% | 3.1% |
| ADFI, lb | 3.35 | 3.38 | 3.39 | 3.39 | 0.05 | 0.79 | 0.9% | 1.2% | 1.2% |
| Feed:Gain | 1.72 | 1.68 | 1.68 | 1.69 | 0.02 | 0.37 | −2.3% | −2.3% | −1.7% |
| D 17-30 | | | | | | | | | |
| ADG, lb | 2.39 | 2.38 | 2.43 | 2.45 | 0.05 | 0.55 | −0.4% | 1.7% | 2.5% |
| ADFI, lb | 4.82 | 4.76 | 4.85 | 4.93 | 0.11 | 0.50 | −1.2% | 0.6% | 2.3% |
| Feed:Gain | 2.02 | 2.00 | 2.00 | 2.01 | 0.03 | 0.94 | −1.0% | −1.0% | −0.5% |
| D 30-43 | | | | | | | | | |
| ADG, lb | 2.57b | 2.55b | 2.62ab | 2.67a | 0.05 | 0.07 | −0.8% | 1.9% | 3.9% |
| ADFI, lb | 5.80b | 5.73b | 5.79b | 6.02a | 0.14 | 0.03 | −1.2% | −0.2% | 3.8% |
| Feed:Gain | 2.26 | 2.24 | 2.22 | 2.25 | 0.03 | 0.72 | −0.9% | −1.8% | −0.4% |
| D 43-56 | | | | | | | | | |
| ADG, lb | 2.58 | 2.65 | 2.60 | 2.65 | 0.05 | 0.23 | 2.7% | 0.8% | 2.7% |
| ADFI, lb | 6.62f | 6.54f | 6.57f | 6.79e | 0.16 | 0.07 | −1.2% | −0.8% | 2.6% |
| Feed:Gain | 2.56a | 2.47b | 2.53ab | 2.56a | 0.03 | 0.07 | −3.5% | −1.2% | 0.0% |
| D 0-30 | | | | | | | | | |
| ADG, lb | 2.14 | 2.18 | 2.20 | 2.21 | 0.03 | 0.23 | 1.9% | 2.8% | 3.3% |
| ADFI, lb | 4.00 | 3.99 | 4.03 | 4.07 | 0.07 | 0.59 | −0.2% | 0.8% | 1.8% |
| Feed:Gain | 1.87 | 1.83 | 1.83 | 1.84 | 0.02 | 0.55 | −2.1% | −2.1% | −1.6% |
| D 30-56 | | | | | | | | | |
| ADG, lb | 2.58 | 2.60 | 2.60 | 2.66 | 0.04 | 0.11 | 0.8% | 0.8% | 3.1% |
| ADFI, lb | 6.21b | 6.13b | 6.18b | 6.40a | 0.15 | 0.03 | −1.3% | −0.5% | 3.1% |
| Feed:Gain | 2.41 | 2.35 | 2.37 | 2.40 | 0.03 | 0.21 | −2.5% | −1.7% | −0.4% |
| D 0-56 | | | | | | | | | |
| ADG, lb | 2.35b | 2.38ab | 2.39ab | 2.42a | 0.03 | 0.08 | 1.3% | 1.7% | 3.0% |
| ADFI, lb | 5.03b | 4.99b | 5.04b | 5.16a | 0.10 | 0.10 | −0.8% | 0.2% | 2.6% |
| Feed:Gain | 2.15 | 2.10 | 2.11 | 2.13 | 0.02 | 0.21 | −2.3% | −1.9% | −0.9% |

(a-c means different superscripts in the same rows are statistically different ($P < 0.05$). e-f means different superscripts in the same rows are statistically different ($P < 0.10$))

Health observations and pig mortality and removal rates are summarized in Table 29. The test pigs remained healthy overall, such that a small number of pigs required medication by injection. With respect to mortality and removal rate, all test pigs fed feed packs had lower mortality and removal rates compared to the control pigs. Particularly, no pig mortalities or removals were observed for pigs fed pack 2 during this study. Packs 1 and 3 numerically reduced mortality and removal rate by 2.4% and 3.6%, respectively, compared to the control (4.8%).

TABLE 29

| Observations | Control | Pack 1 | Pack 2 | Pack 3 |
|---|---|---|---|---|
| Number of pigs | 83 | 83 | 83 | 83 |
| Mortality and Removal, by number of pigs | 4 | 2 | 0 | 3 |
| Number of pigs treated by injection | 2 | 2 | 1 | 2 |

During the overall experimental period (days 0-56), all feed packs performed better than the control on improving ADG and feed efficiency. Among the three packs evaluated, pack 3 performed the best, causing an improvement in ADG by 3.0% and a 4.3 lb. increase in body weight ($P<0.10$). Pack 1 performed the best with respect to feed efficiency, causing a 2.3% increase relative to the control; $P>0.20$). All feed packs tested in this study numerically reduced the mortality and removal rates of pigs.

As used herein, the term "about" modifying, for example, the quantity of a component in a composition, concentration, and ranges thereof, employed in describing the embodiments of the disclosure, refers to variation in the numerical quantity that can occur, for example, through typical measuring and handling procedures used for making compounds, compositions, concentrates, or use formulations; through inadvertent error in these procedures; through differences in the manufacture, source, or purity of starting materials or ingredients used to carry out the methods, and like proximate considerations. The term "about" also encompasses amounts that differ due to aging of a formulation with a particular initial concentration or mixture, and amounts that differ due to mixing or processing a formulation with a particular initial concentration or mixture. Where modified by the term "about" the claims appended hereto include equivalents to these quantities.

Similarly, it should be appreciated that in the foregoing description of example embodiments, various features are sometimes grouped together in a single embodiment for the purpose of streamlining the disclosure and aiding in the understanding of one or more of the various aspects. These methods of disclosure, however, are not to be interpreted as reflecting an intention that the claims require more features than are expressly recited in each claim. Rather, as the following claims reflect, inventive aspects lie in less than all features of a single foregoing disclosed embodiment, and each embodiment described herein may contain more than one inventive feature.

Although the present disclosure provides references to preferred embodiments, persons skilled in the art will recognize that changes may be made in form and detail without departing from the spirit and scope of the invention.

What is claimed is:

1. A method of feeding swine, the method comprising:

feeding the swine a feed composition comprising an active component composition, the active component composition comprising a direct-fed microbial composition and a phytogenic composition, wherein the active component composition constitutes about 0.01 wt % to about 0.5 wt % of the feed composition, the direct-fed microbial composition constitutes greater than 70 wt % of the active component composition, and the phytogenic composition constitutes at least about 24 wt % of the active component composition, wherein the direct-fed microbial composition comprises two strains of *Bacillus pumilus,* wherein the phytogenic composition comprises *Quillaja* and either a combination of *Capsicum annuum* and *Curcuma longa* or a combination of natural essential oils containing thymol and eugenol, wherein the *Quillaja* constitutes about 9 wt % of the active component composition, and wherein the swine ingest about 0.25 grams to about 10 grams of the active component composition per head per day.

2. The method of claim 1, wherein the two strains of *Bacillus pumilus* are included in approximately equal amounts.

3. The method of claim 1, wherein the feed composition further comprises one or more of: ground corn, sugar, dehulled soymeal, soy isolate, hydrolyzed soy protein, dried distillers grains with solubles, poultry byproduct meal, vitamins other than vitamins C and D, or minerals.

4. The method of claim 1, wherein feeding the swine the feed composition results in a reduction in respiratory distress exhibited by the swine.

5. The method of claim 1, wherein feeding the swine the feed composition inhibits *Streptococcus* in the swine.

6. A feed product formulated for swine, the feed product comprising:

a feed composition comprising one or more of: ground corn, sugar, dehulled soymeal, soy isolate, hydrolyzed soy protein, dried distillers grains with solubles, poultry byproduct meal, vitamins other than vitamins C and D, and minerals; and an active component composition comprising:

a direct-fed microbial composition comprising two strains of *Bacillus pumilus*; and a phytogenic blend comprising *Quillaja* and either a combination of *Capsicum annuum* and *Curcuma longa* or a combination of natural essential oils containing thymol and eugenol;

wherein the direct-fed microbial composition constitutes greater than 70 wt % of the active component composition, wherein the phytogenic blend constitutes at least about 24 wt % of the active component composition wherein the *Quillaja* constitutes about 9 wt % of the active component composition, and wherein the active component composition constitutes about 0.01 wt % to about 0.5 wt % of the feed product.

7. The feed product of claim 6, wherein the two strains of *Bacillus pumilus* are included in approximately equal amounts.

* * * * *